United States Patent
Linder et al.

(10) Patent No.: US 12,213,808 B2
(45) Date of Patent: *Feb. 4, 2025

(54) GUIDEWIRE FOR IMAGING AND MEASUREMENT OF PRESSURE AND OTHER PHYSIOLOGICAL PARAMETERS

(71) Applicant: XENTER, INC., Salt Lake City, UT (US)

(72) Inventors: Richard J. Linder, Sandy, UT (US); Edwin Meade Maynard, Salt Lake City, UT (US); Scott Kenneth Marland, Bountiful, UT (US); Cory Rex Estes, Mapleton, UT (US); Steven Matthew Quist, Salt Lake City, UT (US); Nathan J. Knighton, Syracuse, UT (US)

(73) Assignee: XENTER, INC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,136

(22) Filed: Aug. 1, 2023

(65) Prior Publication Data

US 2024/0115205 A1   Apr. 11, 2024

Related U.S. Application Data

(63) Continuation of application No. 17/578,373, filed on Jan. 18, 2022, now Pat. No. 11,751,812, which is a (Continued)

(51) Int. Cl.
*A61B 5/05*   (2021.01)
*A61B 5/00*   (2006.01)
(Continued)

(52) U.S. Cl.
CPC .......... *A61B 5/6852* (2013.01); *A61B 5/0002* (2013.01); *A61B 5/0215* (2013.01);
(Continued)

(58) Field of Classification Search
CPC . A61B 5/0002; A61B 5/0215; A61B 5/02158; A61B 5/0059; A61B 8/12;
(Continued)

(56) References Cited

U.S. PATENT DOCUMENTS

| 4,595,012 A | 6/1986 | Webler et al. |
| 4,827,941 A | 5/1989 | Taylor et al. |

(Continued)

FOREIGN PATENT DOCUMENTS

| CN | 103720463 A | 4/2014 |
| CN | 105212902 A | 1/2016 |

(Continued)

OTHER PUBLICATIONS

Aldaoud, et al. "A stent-based power and data link for sensing intravascular biological indicators." IEEE Sensors Letters 2.4 (2018): 1-4.

(Continued)

*Primary Examiner* — Joel F Brutus
(74) *Attorney, Agent, or Firm* — Workman Nydegger

(57) ABSTRACT

A guidewire system includes an elongated wire configured for insertion into a luminal space, such as the vasculature, of a body. The wire is conductive and configured to conduct electrical signals. One or more sensors are coupled to a distal section of the wire and configured to send and receive the electrical signals via the wire. The wire through which the one or more sensors are coupled is the only wire through which the one or more sensors send and receive the electrical signals.

16 Claims, 14 Drawing Sheets

Related U.S. Application Data continuation of application No. 17/205,964, filed on Mar. 18, 2021, now Pat. No. 11,259,750.

(60) Provisional application No. 63/044,960, filed on Jun. 26, 2020, provisional application No. 62/992,695, filed on Mar. 20, 2020.

(51) Int. Cl.
| | |
|---|---|
| *A61B 5/0215* | (2006.01) |
| *A61B 5/07* | (2006.01) |
| *A61M 25/09* | (2006.01) |
| *H02J 50/05* | (2016.01) |
| *H02J 50/40* | (2016.01) |
| *H02J 50/90* | (2016.01) |
| *A61B 1/05* | (2006.01) |
| *A61B 8/12* | (2006.01) |
| *A61M 25/01* | (2006.01) |

(52) U.S. Cl.
CPC ............ *A61B 5/02158* (2013.01); *A61B 5/07* (2013.01); *A61B 5/6851* (2013.01); *A61M 25/09* (2013.01); *H02J 50/05* (2016.02); *H02J 50/402* (2020.01); *H02J 50/90* (2016.02); *A61B 1/05* (2013.01); *A61B 5/0059* (2013.01); *A61B 8/12* (2013.01); *A61B 2503/40* (2013.01); *A61B 2560/0214* (2013.01); *A61B 2560/0219* (2013.01); *A61B 2562/0247* (2013.01); *A61B 2562/06* (2013.01); *A61B 2562/222* (2013.01); *A61M 2025/0183* (2013.01)

(58) Field of Classification Search
CPC .......... A61B 2562/222; A61B 2562/06; A61B 2562/0247
See application file for complete search history.

(56) References Cited

U.S. PATENT DOCUMENTS

| | | | |
|---|---|---|---|
| 4,850,358 A | 7/1989 | Millar | |
| 4,917,104 A | 4/1990 | Rebell | |
| 5,154,725 A | 10/1992 | Leopold | |
| 5,366,490 A | 11/1994 | Edwards et al. | |
| 5,368,035 A | 11/1994 | Hamm et al. | |
| 5,564,434 A | 10/1996 | Halperin et al. | |
| 5,651,767 A | 7/1997 | Schulman et al. | |
| 5,790,081 A | 8/1998 | Unwin | |
| 5,814,089 A | 9/1998 | Stokes et al. | |
| 5,860,974 A | 1/1999 | Abele | |
| 6,004,269 A | 12/1999 | Crowley et al. | |
| 6,167,763 B1 | 1/2001 | Tenerz et al. | |
| 6,211,799 B1 | 4/2001 | Post et al. | |
| 6,245,020 B1 | 6/2001 | Moore et al. | |
| 6,248,076 B1 | 6/2001 | White et al. | |
| 6,479,785 B1 | 11/2002 | Fugo et al. | |
| 6,728,571 B1 | 4/2004 | Barbato | |
| 7,210,940 B2 | 5/2007 | Baily et al. | |
| 7,645,233 B2 | 1/2010 | Tulkki et al. | |
| 7,651,578 B2 | 1/2010 | Sharrow et al. | |
| 8,076,821 B2 | 12/2011 | Degertekin | |
| 8,277,386 B2 | 10/2012 | Ahmed et al. | |
| 8,362,673 B2 | 1/2013 | Hsu | |
| 8,473,067 B2 | 6/2013 | Hastings et al. | |
| 8,478,384 B2 | 7/2013 | Schmitt et al. | |
| 8,617,088 B2 | 12/2013 | Samuelsson et al. | |
| 8,882,763 B2 | 11/2014 | Stevenson et al. | |
| 9,106,270 B2 | 8/2015 | Puterbaugh et al. | |
| 9,192,306 B2 | 11/2015 | Chen | |
| 9,259,206 B2 | 2/2016 | Degertekin et al. | |
| 9,486,355 B2 | 11/2016 | Gustus et al. | |
| 9,667,323 B2 | 5/2017 | Habraken et al. | |
| 9,675,325 B2 | 6/2017 | Moore et al. | |
| 10,028,667 B2 | 7/2018 | Kishida et al. | |
| 10,080,872 B2 | 9/2018 | Webler | |
| 10,206,556 B2 | 2/2019 | Matsuki et al. | |
| 10,390,791 B2 | 8/2019 | Courtney et al. | |
| 10,391,292 B2 | 8/2019 | Sutton | |
| 10,418,755 B2 | 9/2019 | Kahlman | |
| 10,463,259 B2 | 11/2019 | Glover et al. | |
| 10,463,274 B2 | 11/2019 | Kassab et al. | |
| 10,531,841 B2 | 1/2020 | Merritt et al. | |
| 10,569,072 B2 | 2/2020 | Agrawal et al. | |
| 10,737,086 B2 | 8/2020 | Agrawal et al. | |
| 10,765,853 B2 | 9/2020 | Neff et al. | |
| 10,842,981 B2 | 11/2020 | Agrawal et al. | |
| 10,869,603 B2 | 12/2020 | Millett et al. | |
| 10,881,846 B2 | 1/2021 | Furnish et al. | |
| 11,259,877 B2 | 3/2022 | Kahya et al. | |
| 11,304,659 B2 | 4/2022 | Linder et al. | |
| 2001/0001317 A1 | 5/2001 | Duerig et al. | |
| 2001/0029337 A1 | 10/2001 | Pantages et al. | |
| 2001/0045899 A1 | 11/2001 | Hoek | |
| 2002/0013527 A1 | 1/2002 | Hoek et al. | |
| 2002/0151823 A1 | 10/2002 | Miyata et al. | |
| 2003/0083723 A1 | 5/2003 | Wilkinson et al. | |
| 2003/0120271 A1 | 6/2003 | Burnside et al. | |
| 2004/0064024 A1 | 4/2004 | Sommer | |
| 2004/0153136 A1 | 8/2004 | Vardi et al. | |
| 2005/0143664 A1 | 6/2005 | Chen et al. | |
| 2006/0009817 A1 | 1/2006 | Tulkki | |
| 2006/0264925 A1 | 11/2006 | Sharareh et al. | |
| 2007/0118035 A1 | 5/2007 | Secora | |
| 2007/0191830 A1 | 8/2007 | Crompton et al. | |
| 2007/0233045 A1 | 10/2007 | Weitzner et al. | |
| 2007/0255166 A1 | 11/2007 | Carney et al. | |
| 2008/0021336 A1 | 1/2008 | Dobak, III | |
| 2008/0177183 A1 | 7/2008 | Courtney et al. | |
| 2008/0249515 A1 | 10/2008 | Taylor | |
| 2009/0005859 A1 | 1/2009 | Keilman | |
| 2009/0062739 A1 | 3/2009 | Anderson | |
| 2009/0110148 A1 | 4/2009 | Zhang et al. | |
| 2009/0131798 A1 | 5/2009 | Minar et al. | |
| 2009/0156926 A1 | 6/2009 | Messerly et al. | |
| 2009/0171345 A1 | 7/2009 | Miller et al. | |
| 2009/0259772 A1 | 10/2009 | Ketko et al. | |
| 2009/0284332 A1 | 11/2009 | Moore et al. | |
| 2010/0070007 A1 | 3/2010 | Parker et al. | |
| 2010/0087143 A1 | 4/2010 | Bonin | |
| 2010/0113939 A1 | 5/2010 | Mashimo et al. | |
| 2010/0174233 A1 | 7/2010 | Kuban et al. | |
| 2010/0305476 A1 | 12/2010 | Thornton et al. | |
| 2011/0190756 A1 | 8/2011 | Venkatachalam et al. | |
| 2011/0213220 A1 | 9/2011 | Samuelsson et al. | |
| 2011/0257511 A1 | 10/2011 | Krueger | |
| 2011/0270369 A1 | 11/2011 | Tekmen et al. | |
| 2012/0130230 A1 | 5/2012 | Eichler et al. | |
| 2012/0209061 A1 | 8/2012 | Kato | |
| 2013/0064043 A1 | 3/2013 | Degertekin et al. | |
| 2013/0109980 A1 | 5/2013 | Teo | |
| 2013/0123638 A1 | 5/2013 | Tom et al. | |
| 2013/0172782 A1 | 7/2013 | Hilmersson | |
| 2013/0190726 A1 | 7/2013 | Kesner et al. | |
| 2013/0204111 A1 | 8/2013 | Flanders | |
| 2013/0289424 A1 | 10/2013 | Brockway et al. | |
| 2013/0296692 A1 | 11/2013 | Vanney et al. | |
| 2014/0066705 A1 | 3/2014 | Robertson et al. | |
| 2014/0142398 A1* | 5/2014 | Patil | A61B 5/0538 600/301 |
| 2014/0171788 A1 | 6/2014 | Stigall | |
| 2014/0180031 A1 | 6/2014 | Anderson | |
| 2014/0187978 A1 | 7/2014 | Millett et al. | |
| 2014/0187979 A1 | 7/2014 | Burkett | |
| 2014/0236017 A1 | 8/2014 | Degertekin et al. | |
| 2014/0248801 A1 | 9/2014 | Riezebos et al. | |
| 2014/0323860 A1 | 10/2014 | Courtney et al. | |
| 2015/0074995 A1 | 3/2015 | Patil et al. | |
| 2015/0141854 A1 | 5/2015 | Eberle et al. | |
| 2015/0196210 A1 | 7/2015 | McCaffrey | |
| 2015/0208901 A1 | 7/2015 | Gazdzinski | |
| 2015/0216403 A1 | 8/2015 | Whitmore | |

(56) References Cited

U.S. PATENT DOCUMENTS

| | | |
|---|---|---|
| 2015/0265181 A1 | 9/2015 | Flanders |
| 2015/0305708 A1 | 10/2015 | Stigall et al. |
| 2015/0313478 A1 | 11/2015 | Veszelei et al. |
| 2016/0249817 A1 | 9/2016 | Mazar et al. |
| 2016/0262698 A1 | 9/2016 | Mahlin |
| 2016/0310020 A1 | 10/2016 | Warnking et al. |
| 2017/0136496 A1 | 5/2017 | Jacobs et al. |
| 2017/0164867 A1 | 6/2017 | Kassab et al. |
| 2017/0164925 A1 | 6/2017 | Marshall et al. |
| 2017/0189669 A1 | 7/2017 | Kamarajugadda et al. |
| 2017/0215801 A1 | 8/2017 | Jung et al. |
| 2017/0266433 A1 | 9/2017 | Daniels et al. |
| 2018/0099125 A1 | 4/2018 | Richer et al. |
| 2018/0125365 A1 | 5/2018 | Hunter et al. |
| 2018/0262236 A1 | 9/2018 | Kahlman |
| 2018/0263515 A1 | 9/2018 | Raval |
| 2019/0053787 A1 | 2/2019 | Stigall et al. |
| 2019/0070402 A1 | 3/2019 | Isaacson |
| 2019/0133462 A1 | 5/2019 | Millett et al. |
| 2019/0167351 A1 | 6/2019 | Salazar et al. |
| 2019/0184159 A1 | 6/2019 | Yeh et al. |
| 2019/0247618 A1 | 8/2019 | Shellhammer et al. |
| 2019/0290139 A1 | 9/2019 | Sio et al. |
| 2019/0290368 A1* | 9/2019 | West ................. A61B 34/20 |
| 2019/0298182 A1 | 10/2019 | Syed et al. |
| 2019/0358387 A1 | 11/2019 | Elbadry et al. |
| 2019/0380651 A1 | 12/2019 | Carreel et al. |
| 2020/0022587 A1 | 1/2020 | Glover et al. |
| 2020/0054227 A1 | 2/2020 | Van Rens |
| 2020/0060577 A1 | 2/2020 | Kassab et al. |
| 2021/0030364 A1 | 2/2021 | Burkett et al. |
| 2021/0290059 A1 | 9/2021 | Linder et al. |
| 2021/0290100 A1 | 9/2021 | Linder et al. |
| 2021/0290164 A1 | 9/2021 | Linder et al. |
| 2021/0290198 A1 | 9/2021 | Linder et al. |
| 2022/0047845 A1 | 2/2022 | Niederhauser et al. |
| 2022/0133236 A1 | 5/2022 | Linder et al. |
| 2022/0160306 A1 | 5/2022 | Linder et al. |
| 2022/0202368 A1 | 6/2022 | Linder et al. |
| 2022/0361743 A1 | 11/2022 | Chan et al. |
| 2023/0109126 A1 | 4/2023 | Linder et al. |

FOREIGN PATENT DOCUMENTS

| | | |
|---|---|---|
| CN | 105919559 | 9/2016 |
| DE | 19621003 | 1/1997 |
| JP | 09-512470 A | 12/1997 |
| JP | 2014-530639 A | 11/2014 |
| JP | 2015-501193 A | 1/2015 |
| JP | 2015-061314 A | 3/2015 |
| JP | 2016-509497 A | 3/2016 |
| JP | 2017-501755 A | 1/2017 |
| JP | 2016-518870 A | 3/2017 |
| JP | 2017-508574 A | 3/2017 |
| JP | 2018-524076 A | 8/2018 |
| JP | 2018-140180 A | 9/2018 |
| WO | 2012/173697 A1 | 12/2012 |
| WO | 2016/130713 A1 | 8/2016 |
| WO | 2016/209665 A1 | 12/2016 |
| WO | 2018/017547 | 1/2018 |
| WO | 2020/030776 A1 | 2/2020 |

OTHER PUBLICATIONS

Degertekin FL, Guldiken RO, Karaman M. Annular-ring CMUT arrays for forward-looking IVUS: transducer characterization and imaging. IEEE Trans Ultrason Ferroelectr Freq Control. Feb. 2006;53(2):474-82.

E. F. Arkan and F. L. Degertekin, "Analysis and Design of High-Frequency 1-D CMUT Imaging Arrays in Noncollapsed Mode," in IEEE Transactions on Ultrasonics, Ferroelectrics, and Frequency Control, vol. 66, No. 2, pp. 382-393, Feb. 2019.

Final Office Action received for U.S. Appl. No. 17/205,754, mailed on Aug. 25, 2021, 12 pages.

Final Office Action received for U.S. Appl. No. 17/205,854, mailed on Sep. 23, 2021, 14 pages.

G. Jung, C. Tekes, A. Pirouz, F. L. Degertekin and M. Ghovanloo, "Supply-Doubled Pulse-Shaping High Voltage Pulser for CMUT Arrays," in IEEE Transactions on Circuits and Systems II: Express Briefs, vol. 65, No. 3, pp. 306-310, Mar. 2018.

Gurun G, Hasler P, Degertekin F. Front-end receiver electronics for high-frequency monolithic CMUT-on-CMOS imaging arrays. IEEE Transactions on Ultrasonics, Ferroelectrics, and Frequency Control. Aug. 2011;58(8):1658-1668.

Gurun G, Tekes C, Zahorian J, Xu T, Satir S, Karaman M, Hasler J, Degertekin FL. Single-chip CMUT-on-CMOS front-end system for real-time volumetric IVUS and ICE imaging. IEEE Trans Ultrason Ferroelectr Freq Control. Feb. 2014;61(2):239-50.

J. Lim, C. Tekes, E. F. Arkan, A. Rezvanitabar, F. L. Degertekin and M. Ghovanloo, "Highly Integrated Guidewire Ultrasound Imaging System-on-a-Chip," in IEEE Journal of Solid-State Circuits, vol. 55, No. 5, pp. 1310-1323, May 2020.

J. Lim, C. Tekes, F. L. Degertekin and M. Ghovanloo, "Towards a Reduced-Wire Interface for CMUT-Based Intravascular Ultrasound Imaging Systems," in IEEE Transactions on Biomedical Circuits and Systems, vol. 11, No. 2, pp. 400-410, Apr. 2017.

J. Zahorian et al., "Monolithic CMUT-on-CMOS Integration for Intravascular Ultrasound Applications," in IEEE Transactions on Ultrasonics, Ferroelectrics, and Frequency Control, vol. 58, No. 12, pp. 2659-2667, Dec. 2011.

Lim J, Arkan EF, Degertekin FL, Ghovanloo M. Toward a reduced-wire readout system for ultrasound imaging. Annu Int Conf IEEE Eng Med Biol Soc. 2014;2014:5080-4.

Lim J, Rezvanitabar A, Degertekin FL, Ghovanloo M. An Impulse Radio PWM-Based Wireless Data Acquisition Sensor Interface. IEEE Sens J. Jan. 15, 2019;19(2):603-614.

Lu, et al. "A review on the recent development of capacitive wireless power transfer technology." Energies 10.11 (2017): 1752.

Non-Final Office Action received for U.S. Appl. No. 17/205,854, mailed on May 19, 2022, 17 pages.

Non-Final Office Action received for U.S. Appl. No. 17/578,373, mailed on Dec. 30, 2022, 11 pages.

Non-Final Office Action received for U.S. Appl. No. 17/205,964, mailed on May 24, 2021.

Pirouz, A.; Degertekin, F.L. An Analysis Method for Capacitive Micromachined Ultrasound Transducer (CMUT) Energy Conversion during Large Signal Operation. Sensors 2019, 19, 876.

S. Satir and F. L. Degertekin, "A nonlinear lumped model for ultrasound systems using CMUT arrays," in IEEE Transactions on Ultrasonics, Ferroelectrics, and Frequency Control, vol. 62, No. 10, pp. 1865-1879, Oct. 2015.

S. Satir, J. Zahorian and F. L. Degertekin, "A large-signal model for CMUT arrays with arbitrary membrane geometry operating in non-collapsed mode," in IEEE Transactions on Ultrasonics, Ferroelectrics, and Frequency Control, vol. 60, No. 11, pp. 2426-2439, Nov. 2013.

Satir S, Degertekin FL. Phase and Amplitude Modulation Methods for Nonlinear Ultrasound Imaging With CMUTs. IEEE Trans Ultrason Ferroelectr Freq Control. Aug. 2016;63(8):1086-92.

Sharei, et al. "Data communication pathway for sensing guidewire at proximal side: A review." Journal of Medical Devices 11.2 (2017).

Tanase et al. "Multi-parameter sensor system with intravascular navigation for catheter/guide wire application", Sensors and Actuators A: Physical vols. 97-98, Apr. 1, 2002, pp. 116-124.

Tekes C, Zahorian J, Gurun G, et al. Volumetric imaging using single chip integrated CMUT-on-CMOS IVUS array. Annu Int Conf IEEE Eng Med Biol Soc. 2012;2012:3195-3198.

International Search Report and Written Opinion received for PCT Patent Application No. PCT/US21/023198, mailed on Jun. 14, 2021, 2 pages.

International Search Report and Written Opinion received for PCT Patent Application No. PCT/US21/23135, mailed on Jun. 8, 2021, 8 pages.

(56) References Cited

OTHER PUBLICATIONS

International Search Report and Written Opinion received for PCT Patent Application No. PCT/US21/23148, mailed on Jun. 4, 2021, 7 pages.
International Search Report and Written Opinion received for PCT Patent Application No. PCT/US21/23184, mailed on Jun. 7, 2021, 10 pages.
Non-Final Office Action received for U.S. Appl. No. 18/074,126, mailed on May 7, 2024, 13 pages.

* cited by examiner

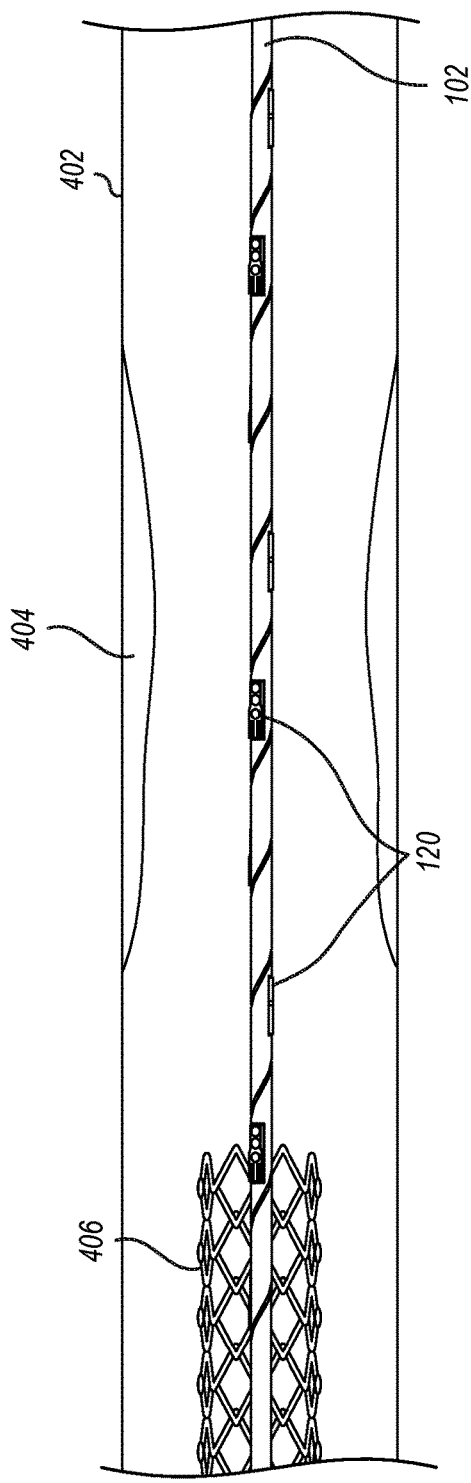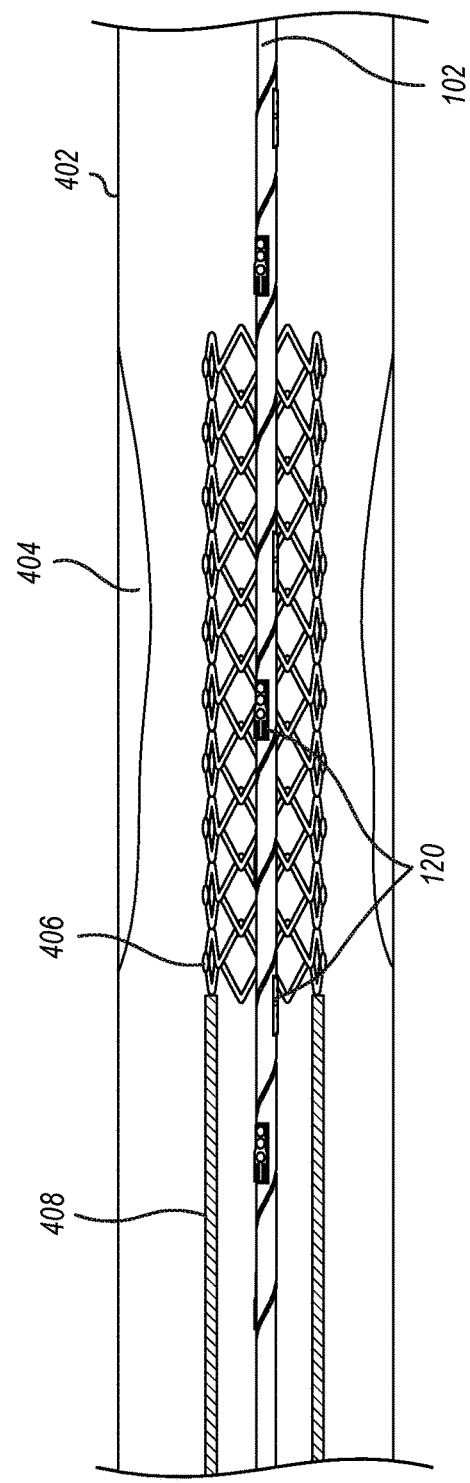
FIG. 4A
FIG. 4B

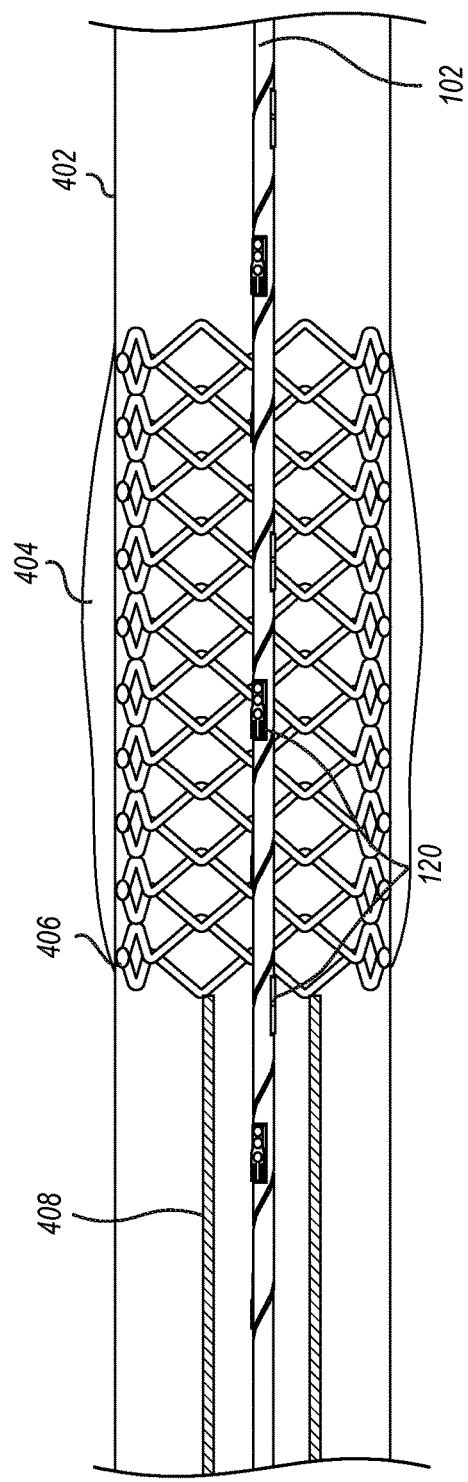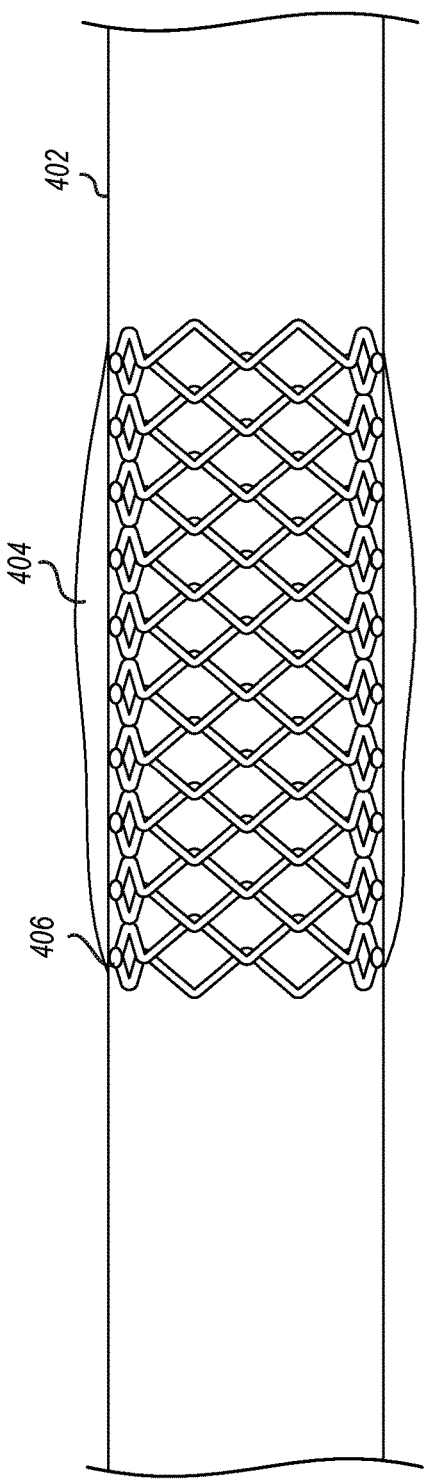

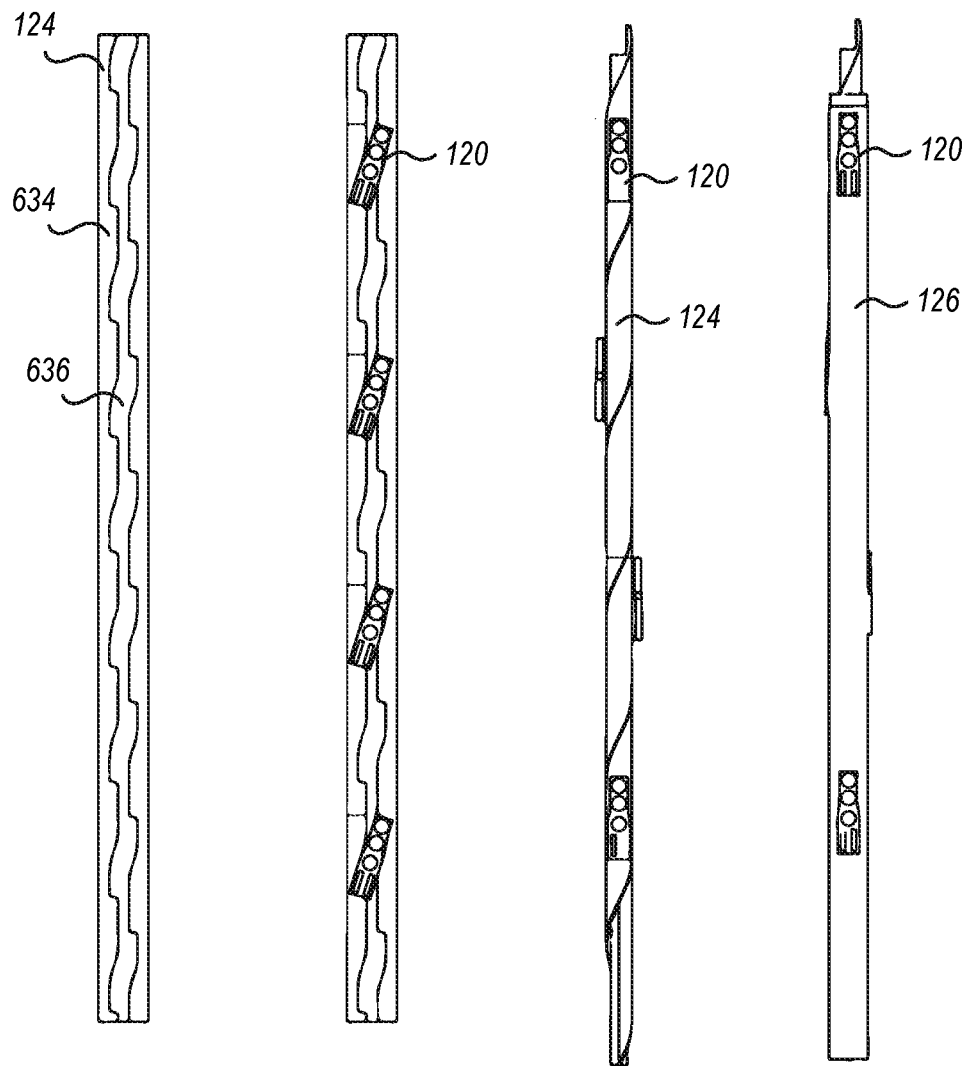
FIG. 6A  FIG. 6B  FIG. 6C  FIG. 6D

GUIDEWIRE FOR IMAGING AND MEASUREMENT OF PRESSURE AND OTHER PHYSIOLOGICAL PARAMETERS

CROSS-REFERENCE TO RELATED APPLICATIONS

This application is a continuation of U.S. patent application Ser. No. 17/578,373, filed on Jan. 18, 2022, and titled "GUIDEWIRE FOR IMAGING AND MEASUREMENT OF PRESSURE AND OTHER PHYSIOLOGICAL PARAMETERS," which is a continuation of U.S. patent application Ser. No. 17/205,964, filed Mar. 18, 2021, now issued under U.S. Pat. No. 11,295,750 issued on Mar. 1, 2022 and titled "GUIDEWIRE FOR IMAGING AND MEASUREMENT OF PRESSURE AND OTHER PHYSIOLOGICAL PARAMETERS," which claims priority to U.S. Provisional Patent Application Ser. No. 62/992,695, filed Mar. 20, 2020 and titled "CATHETER SYSTEM, DEVICE, AND METHOD THEREOF," and to U.S. Provisional Patent Application Ser. No. 63/044,960, filed Jun. 26, 2020 and titled "CATHETER AND GUIDEWIRE SYSTEMS WITH ENHANCED LOCATION AND CHARACTERIZATION FEATURES." The entire content of each of the foregoing are incorporated herein by reference.

Additionally, the present application is related to U.S. patent application Ser. No. 17/205,614, filed Mar. 18, 2021 and titled "SIGNAL CONDUCTING DEVICE FOR CONCURRENT POWER AND DATA TRANSFER TO AND FROM UN-WIRED SENSORS ATTACHED TO A MEDICAL DEVICE," U.S. patent application Ser. No. 17/205,754 filed Mar. 18, 2021 and titled "OPERATIVELY COUPLED DATA AND POWER TRANSFER DEVICE FOR MEDICAL GUIDEWIRES AND CATHETERS WITH SENSORS," and U.S. patent application Ser. No. 17/205,854 filed Mar. 18, 2021 and titled "CATHETER FOR IMAGING AND MEASUREMENT OF PRESSURE AND OTHER PHYSIOLOGICAL PARAMETERS." Each of the foregoing applications is incorporated herein in its entirety.

BACKGROUND

The present invention relates generally to medical devices, including intraluminal devices such as guidewires and catheters that include various sensors for simultaneous and/or continuous measuring of one or more physiological parameters.

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. Guidewires are available with various outer diameter sizes. Widely utilized sizes include 0.010, 0.014, 0.016, 0.018, 0.024, and 0.035 inches in diameter, for example, though they may also be smaller or larger in diameter.

In many instances, a guidewire is placed within the body during the interventional procedure where it can be used to guide multiple catheters or other interventional devices to the targeted anatomical location. Once in place, a catheter can be used to aspirate clots or other occlusions, or to deliver drugs, stents, embolic devices, radiopaque dyes, or other devices or substances for treating the patient.

These types of interventional devices can include sensors located at the distal end in order to provide added functionality to the device. For example, intravascular ultrasound (IVUS) is an imaging technique that utilizes a catheter with an ultrasound imaging sensor attached to the distal end. Ultrasound is utilized to image within targeted vasculature (typically the coronary arteries).

The use of such sensors introduces several challenges. In particular, the interventional devices involved have very limited space to work in, given the stringent dimensional constraints involved. Moreover, integrating the sensors with the interventional device in a way that maintains effective functionality can be challenging.

Another issue common to the field is proper localization and positioning of the distal end of the device at the target location. If the device tip is improperly positioned during insertion, or if the tip migrates away from the desired position after insertion, various risks can arise. For catheter implementations, for example, improper positioning can lead to fluid infusions that can cause pain or injury to the patient, increased thrombosis rates, delays in therapy, device breakage or malfunction, delays due to device replacement, and additional costs associated with the device replacement and the additional time required by the attending physician and the medical center.

Further, conventional approaches to internal imaging and catheter localization require the injection of dye and/or the use of X-rays. Each of these can be harmful to the subject. In addition, such imaging radiation can be harmful to the physicians and staff exposed to the radiation.

The use of such interventional devices is also challenging due to the need to manage several long lengths of wires and other components, including guidewires, power cables, data wires, and the like. Care must be taken with respect to what is allowed in the sterile field and when it can be removed. Additional staff is often required simply to manage such wires and cables.

As such, there is an ongoing need for improved interventional devices that effectively integrate sensors, effectively manage power and data communication with the sensors, effectively communicate data off of the device for additional processing, and that enable more effective positioning of the medical device in the desired target position within the vasculature or other targeted anatomy.

SUMMARY

In one embodiment, a guidewire system includes an elongated wire configured for insertion into a luminal space, such as the vasculature, of a body. The wire is conductive and configured to conduct electrical signals. One or more sensors are coupled to a distal section of the wire and configured to send and receive the electrical signals via the wire. The wire through which the one or more sensors are coupled is the only wire through which the one or more sensors send and receive the electrical signals.

The one or more sensors may include two or more different sensors types, such as pressure sensors and ultrasound sensors. When multiple sensors are utilized, the guidewire system is configured to provide simultaneous measurement of one or more physiological parameters. That is, multiple sensors (which may be of more than one type) positioned at multiple positions can simultaneously send sensor data through the wire.

The guidewire system may include a proximal device operatively coupled to the wire at a proximal section of the wire and configured to communicate with the one or more sensors positioned at a distal section of the wire via the electrical signals passed through the wire. For example, the proximal device may be configured to send power to the one or more sensors through the wire and to receive data signals from the one or more sensors through the wire.

In some embodiments, the one or more sensors are coupled to a substrate, and wherein the substrate is coupled to a distal section of the wire. For example, the substrate may be wrapped around the distal section of the core. In some embodiments, the substrate is wrapped around the distal section of the core in a spiral fashion. In some embodiments, the substrate includes an elongated tube having a cut pattern that allows radial expansion of the tube to allow the tube to be positioned over the desired section of the wire before the tube reverts to a default shape of smaller diameter.

In one embodiment, a method of using a guidewire system includes: positioning, within a luminal space of a body, a first member, the first member comprising an elongated wire, the wire having a proximal portion and a distal portion and the wire being configured to conduct electrical signals; coupling an electrical signal to the wire; and sending and receiving the electrical signal via the wire from one or more sensors of one or more sensor types coupled to the distal portion of the wire.

The method may also include: placing a second member (e.g., a catheter) over or adjacent to the wire; translating the second member with respect to the wire such that the second member is moved into the body; translating the second member over the one or more sensors of one or more sensor types; and receiving data signals from the one or more sensors indicating a relative location of the second member within the body with respect to the one or more sensors. The one or more sensors may include, for example, multiple pressure sensors aligned at multiple different longitudinal locations along the distal portion of the wire.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIGS. 4A-4D illustrate an exemplary use of the guidewire system to effectively guide positioning and deployment of a stent at a targeted stenosis;

FIGS. 6A-6D illustrate a process for applying a sensor substrate to the distal section of the guidewire;

DETAILED DESCRIPTION

Overview of Intraluminal Systems

Figure 1:
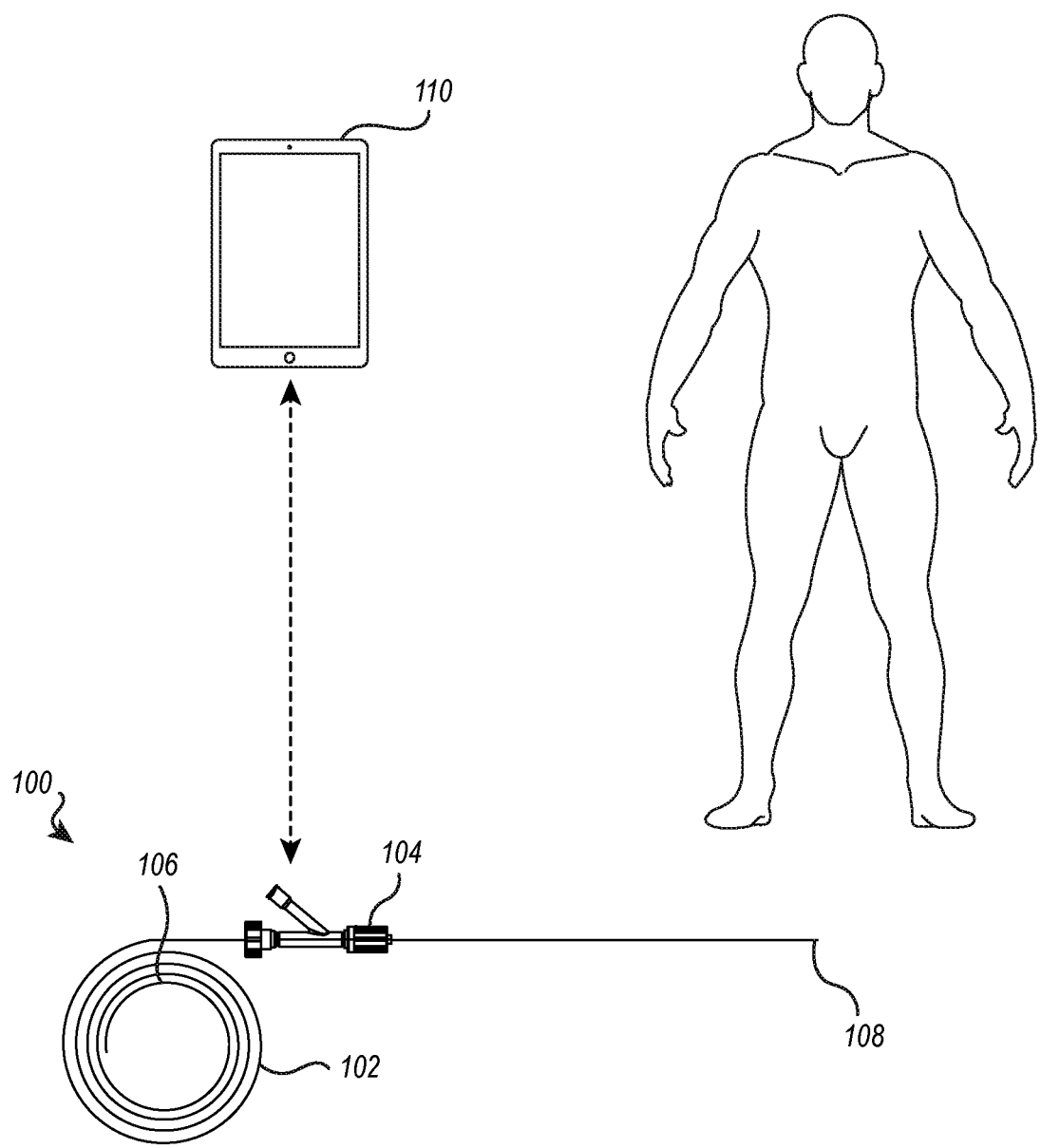
FIG. 1 illustrates a schematic overview of a guidewire system configured to provide one or more of the features described herein.

FIG. 1 illustrates a schematic overview of a guidewire system 100 that may incorporate one or more of the features described herein. The guidewire system 100 includes an elongated wire 102 that is routable through a proximal device 104. The guidewire system 100 may sometimes be alternatively referred to herein as the "guidewire device" or simply "the device". As used herein, the wire 102 may also be referred to as a type of elongated conductive member.

As used herein, the elongated conductive member comprises any conductive component that is longer than it is wide. For example, the elongated conductive member includes the wire 102. For the sake of example and explanation, the elongated conductive member may also be referred to as the wire 102; however, one will appreciate the wire 102 is a subset of possible elongated conductive members. For example, the elongated member may also comprise catheter 202.

The "wire" of the guidewire system 100 refers to the solid wire element that forms the backbone of the guidewire system 100. The term "wire", when used in the context of the guidewire system 100, is therefore intended to refer to a structure that has sufficient characteristics of torqueability, pushability, and stiffness/flexibility to be navigable within a body (e.g., capable of being routed through and positioned within a luminal space such as the vasculature). Such a "wire" element is sometimes referred to in the art as a "core", "core wire", or the like. This type of "wire" is therefore intended to be distinguished from smaller, less structured elements such as traces or leads that are capable of carrying an electrical signal but lack sufficient structure to be effectively navigated and positioned within the body to reach targeted anatomy. As an example, a "wire" suitable for use as part of the guidewire system 100 can have an average outside diameter of at least about 0.003 inches, or about 0.005 inches, or about 0.008 inches, or about 0.010 inches.

In another example, a "wire" suitable for use as part of the guidewire system 100 can have a yield strength above 10 ksi, or more preferably above 30 ksi, or more preferably above 50 ksi, or more preferably above 100 ksi, or more preferably above 150 ksi, or more preferably above 200 ksi, or more preferably above 250 ksi, such as about 300 ksi. Additionally, or alternatively, the "wire" suitable for use as part of the guidewire system 100 can have a shear modulus above 6.7 msi, or more preferably above 8 msi, or more preferably above 10 msi, such as about 12 msi. Additionally, or alternatively, the "wire" suitable for use as part of the guidewire system 100 can have a modulus of elasticity of above 16 msi, or more preferably above 20 msi, or more preferably above 25 msi, such as about 30 msi.

The wire 102 of the guidewire system 100 is configured for insertion into the body of a subject. The subject is typically a human, but in other implementations may be a non-human mammal or even non-mammalian animal. Any suitable route of administration may be utilized, depending on particular preferences and/or application needs. Common routes include femoral, radial, and jugular, but the guidewire system 100 may utilize other access routes as needed.

Although many of the examples described herein relate to use of the guidewire system 100 or the catheter system 200 (see FIG. 2) in relation to intravascular procedures (e.g., cardiovascular or neurovascular), it will be understood that the described systems may be utilized in other medical applications as well. Other medical applications where the systems described herein may be utilized include, for example, applications involving access of the lymphatic, urinary/renal, gastrointestinal, reproductive, hepatic, or respiratory systems.

The proximal device 104 is shown here as a hemostatic valve, though in other embodiments the proximal device 104 may include additional or alternative forms. The proximal device 104 may also be referred to herein as the "power and data coupling device 104" or simply the "coupling device 104".

The wire 102 has a proximal end 106 and a distal end 108. The length of the wire 102 may vary according to particular application needs and targeted anatomical area. As an example, the wire 102 may have an overall length from proximal end 106 to distal end 108 of about 50 cm to about 350 cm, more commonly about 200 cm, depending on particular application needs and/or particular anatomical targets. The wire 102 may have a size such that the outer diameter (e.g., after application of other outer members) is about 0.008 inches to about 0.040 inches, though larger or smaller sizes may also be utilized depending on particular application needs. For example, particular embodiments may have outer diameter sizes corresponding to standard guidewire sizes such as 0.010 inches, 0.014 inches, 0.016 inches, 0.018 inches, 0.024 inches, 0.035 inches, 0.038 inches, or other such sizes common to guidewire devices. The wire 102 may be formed from stainless steel or other metal or alloy having similar appropriate properties. In some embodiments, the wire 102 may be formed of or may comprise a conductive material of appropriate mechanical properties.

The coupling device may also include or be associated with a transmitter to enable wireless communication between the guidewire system 100 and an external device 110 (or multiple such external devices). In alternative embodiments, the guidewire system 100 and external device 110 may be connected via a wired connection.

The external device 110 may be a hand-held device, such as a mobile phone, tablet, or lap-top computer. Although exemplary embodiments are described herein as using hand-held or mobile devices as the external devices 110, it will be understood that this is not necessary, and other embodiments may include other "non-mobile" devices such as a desktop computer, monitor, projector, or the like. In some embodiments, the external device 110 includes a mobile/hand-held device and additionally includes a desktop device or other non-mobile device. For example, a mobile device may be configured to receive transmitted data from the transmitter and function as a bridge by further sending the data to the non-mobile computer system. This may be useful in a situation where the physician would like the option of viewing data on a mobile device, but may need to have the data additionally or alternatively passed or mirrored on a larger monitor such as when both hands are preoccupied (e.g., while handling the guidewire system 100).

The external device 110 of the guidewire system 100 may assist the physician in determining a position of the distal tip of the wire 102 within a vessel or other targeted anatomy of the human body. In this manner, the physician can appropriately position the wire 102 while also obtaining data of various parameters at the targeted anatomy so that the physician can better understand the relevant environment and make appropriate decisions while treating a patient.

The wireless system(s) may include, for example, a personal area network (PAN) (e.g., ultra-high frequency radio wave communication such as Bluetooth®, ZigBee®, BLE, NFC), a local area network (LAN) (e.g., WiFi), or a wide area network (WAN) (e.g., cellular network such as 3G, LTE, 5G). Wireless data transmission may additionally or alternatively include the use of light signals (infrared, visible radio, with or without the use of fiber optic lines), such as radiofrequency (RF) sensors, infrared signaling, or other means of wireless data transmission.

As used herein, "electrical signals" and "signals" both refer generally to any signal within a disclosed system, device, or method. Whereas, "sensor data signal," "sensor signal," or "data signal" refers to any signal that carries commands or information generated by a medical device, such as a medical sensor. In contrast, "power signal" or "energy signal" refers to any signal that provides power to a medical device, such as a sensor. In some cases, a "signal" may comprise both a data signal and a power signal.

Processing of sensor data signals may be fully or primarily carried out at the external device 110, or alternatively may be at least partially carried out at one or more other external devices communicatively connected to the external device 110, such as at a remote server or distributed network. Additionally, or alternatively, sensor data signals may be processed at the coupling device 104, on the wire 102, or at some combination of devices within the guidewire system 100. Sensor data signals may include, for example, image data, location data, and/or various types of sensor data (as related to fluid flow, fluid pressure, presence/levels of various gases or biological components, temperature, other physical parameters, and the like).

As explained in greater detail below, one or more sensors may be coupled to the wire 102, and the one or more sensors can operate to send data signals through the wire 102 to the coupling device 104. Additionally, or alternatively, the coupling device 104 may operate to send power or signals to the one or more sensors.

Figure 2:
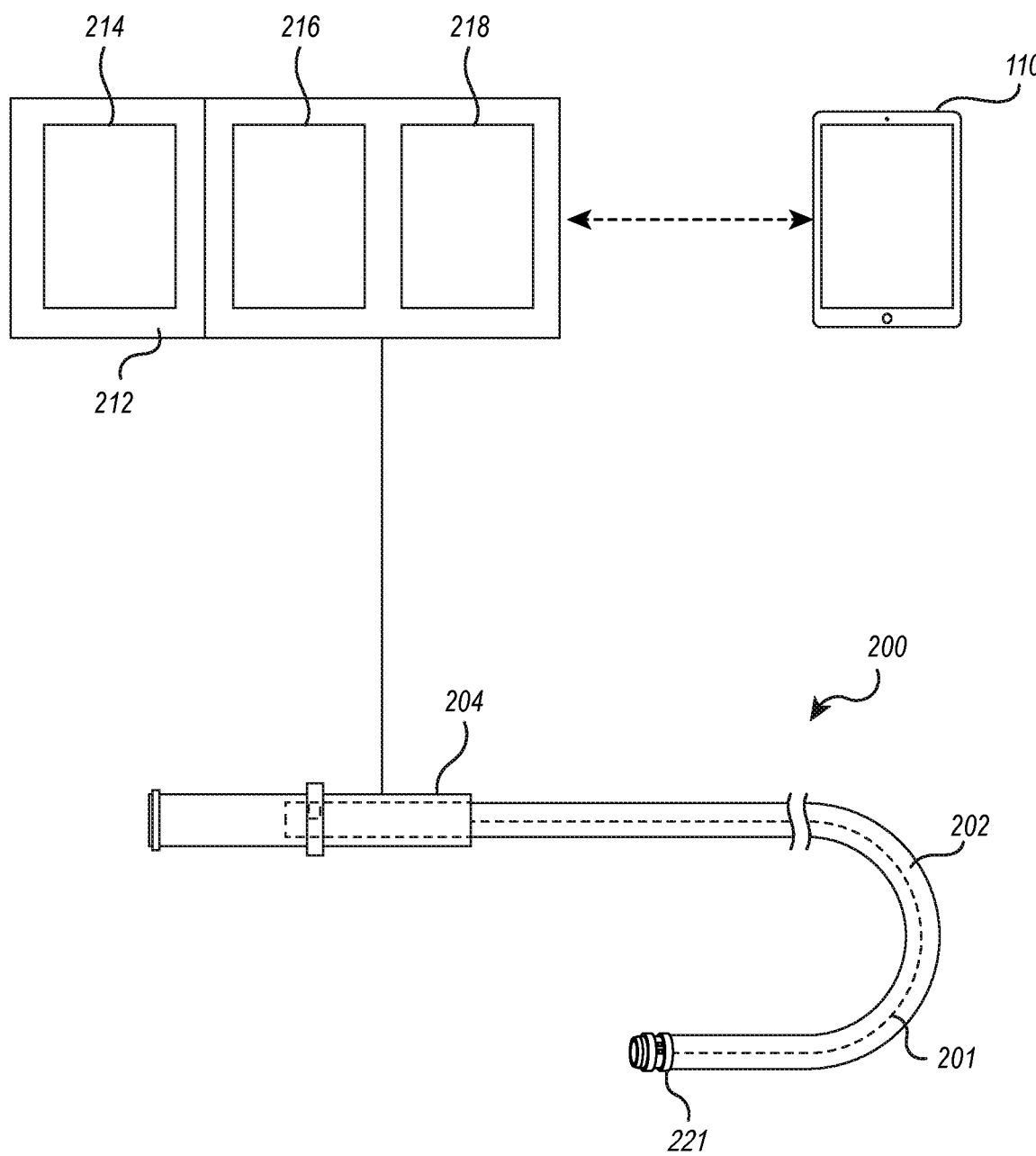
FIG. 2 illustrates a catheter system configured to provide one or more of the features described herein, showing components of a power and data coupling device and showing that the coupling device may be communicatively coupled to an external device.

FIG. 2 is an overview of a catheter system 200 that may incorporate one or more of the features described herein. The catheter system 200 may be similar to the guidewire system 100 in many respects, and the above description related to the guidewire system 100 is also applicable here except where differences are specified.

The catheter system 200 includes a catheter 202 and a proximal device 204 (which may also be referred to herein as "the power and data coupling device 204" or just "the coupling device 204"). The coupling device 204 includes a control unit 212 (shown enlarged and in schematic form) that includes a power source 214, data signal processor 216, and optionally a transmitter 218. The transmitter 218 enables wireless communication to the external device 110 (or multiple such devices) as described above with respect to FIG. 1. As used herein, the catheter 202 may also be referred to as a type of elongated conductive member.

The data signal processor 216 is configured to receive sensor data signals, sent through the catheter 202, from one or more sensors 221 associated with the catheter 202. The power source 214 is configured to transmit power through the catheter 202 to power the one or more sensors 221 and/or other components of the catheter 202. The power source 214 may include an on-board power source, such as a battery or battery pack, and/or may include a wired connection to an outside power source. The one or more sensors 221 may be located at any suitable position on the catheter 202, but will typically be disposed at the distal section of the catheter 202 expected to reach the targeted anatomy. Sensors 221 may be coupled to the catheter 202 by employing bonding, molding, co-extrusion, welding and/or gluing techniques, for example.

Power wires and/or data lines 201 extend along the length of the catheter 202 to the one or more sensors 221. As used herein, a "power line" and/or "data line" refer to any electrically conductive pathway (e.g., traces) within the medical device. Although multiple power and/or data lines 201 may be utilized, preferred embodiments are configured to send both power and data on a single line and/or manage sensor data signals from multiple sensors on a single line. This reduces the number of lines that must be routed through the structure of the catheter 202 and more effectively utilizes the limited space of the device, as well as reducing the complexity of the device and the associated risk of device failure.

The proximal device 204 may include one or more ports to facilitate the introduction of fluids (e.g., medications, nutrients) into the catheter 202. The catheter 202 may be sized and configured to be temporarily inserted in the body, permanently implanted in the body, or configured to deliver an implant in the body. In one embodiment, the catheter 202 is a peripherally inserted central catheter (PICC) line, typically placed in the arm or leg of the body to access the vascular system of the body. The catheter 202 may also be a central venous catheter, an IV catheter, coronary catheter, stent delivery catheter, balloon catheter, atherectomy type catheter, or IVUS catheter or other imaging catheter. The catheter 202 may be a single or multi-lumen catheter.

Figure 3A:
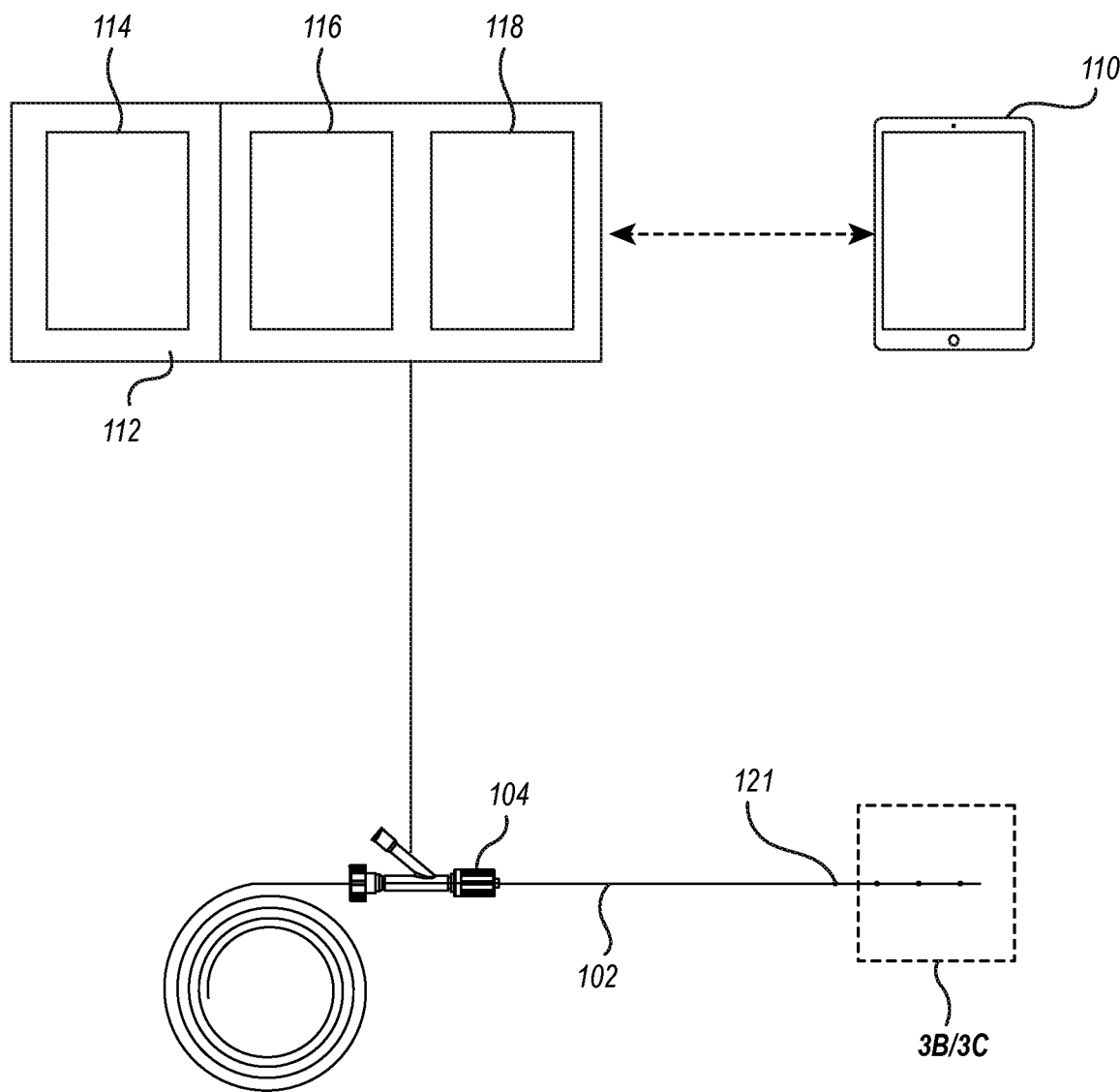
FIG. 3A illustrates a more detailed view of the guidewire system of FIG. 1, showing components of a power and data coupling device and showing that the coupling device may be communicatively coupled to an external device.

FIG. 3A provides another view of the guidewire system 100 of FIG. 1. The guidewire system 100 shares certain features with the catheter system 200, and the description of common parts is therefore applicable to the guidewire system 100 as well. As shown, the guidewire system 100 includes a control unit 112 (shown enlarged and in schematic form) that includes a power source 114, data signal processor 116, and optionally a transmitter 118. The transmitter 118 enables wireless communication to the external device 110 (or multiple such devices) as described above.

The data signal processor 116 is configured to receive sensor data signals, sent through the wire 102, from one or more sensors 121 associated with the wire 102. The power source 114 is configured to transmit power through the wire 102 to power the one or more sensors 121 and/or other components of the wire 102. The power source 114 may include an on-board power source, such as a battery or battery pack, and/or may include a wired connection to an outside power source. The one or more sensors 121 may be located at any suitable position on the wire 102, but will typically be disposed at the distal section expected to reach the targeted anatomy. As used herein, the "distal section" or "distal portion" refers to the distal-most 30 cm of the device, the distal-most 20 cm of the device, the distal-most 15 cm of the device, the distal-most 10 cm of the device, or to a range using any two of the foregoing values as endpoints. In some embodiments, the "intermediate section" may be considered as roughly the middle third of the device, and the "proximal section" or "proximal portion" may be considered as roughly the proximal third of the device.

Unlike the catheter system 200, the guidewire system 100 is configured to send these power and data signals through the actual wire 102 itself. In some embodiments, multiple power and/or data signals (e.g., data signals from multiple sensors 121) can be sent through the wire 102 simultaneously. Power and/or data signals can also be sent in a "continuous" fashion. That is, the power and/or data signals can have a sufficiently high sampling rate such that the information is provided to the user within time frames that are practically "real-time". For most applications, this will include sampling rates (e.g., when active) of approximately 5 seconds or less, 3 seconds or less, 1 second or less, or sub-second sampling rates.

Using the wire 102 itself to send power and/or data signals through the device provides several benefits. For example, using the wire 102 to transmit these signals reduces or eliminates the need to run other connection lines along the wire 102 to connect the sensors 121 to the proximal end and/or to deliver power to the sensors. Given the fact that guidewires inherently involve strict dimensional and performance (e.g., torqueability, bending, pushability, stiffness, etc.) limitations and have limited space to work in, the ability to reduce or eliminate extraneous components frees up limited space and allows greater design flexibility. Reducing or eliminating the use of additional connection lines also reduces the overall complexity of the device and thereby reduces the risk of component failure, leading to a more robustly functional device.

Additional Sensor Details

The one or more sensors 121 of the guidewire system 100 and/or the one or more sensors 221 of the catheter system 200 may include a pressure sensor, flow sensor, imaging sensor, or a component detection sensor, for example. A pressure sensor (or multiple pressure sensors) may be sized and configured to sense changes in pressure in the environment. A flow sensor (or multiple flow sensors) may be sized and configured to sense the fluid flow, such as velocity or other flow characteristics. A detection sensor (or multiple detection sensors) may detect a proximity or distance to one or more detection nodes positioned external relative to the body. An imaging sensor may gather various forms of imaging data.

The one or more sensors may be additionally or alternatively be configured to sense the presence of biological components or measure physiological parameters in the targeted anatomical location (e.g., in the blood). Example biological components that may be detected/measured include sugar levels, pH levels, $CO_2$ levels ($CO_2$ partial pressure, bicarbonate levels), oxygen levels (oxygen partial pressure, oxygen saturation), temperature, and other such substrates and physiological parameters. The one or more sensors may be configured to sense the presence, absence, or levels of biological components such as, for example, immune system-related molecules (e.g., macrophages, lymphocytes, T cells, natural killer cells, monocytes, other white blood cells, etc.), inflammatory markers (e.g., C-reactive protein, procalcitonin, amyloid A, cytokines, alpha-1-acid glycoprotein, ceruloplasmin, hepcidin, haptoglobin, etc.), platelets, hemoglobin, ammonia, creatinine, bilirubin, homocysteine, albumin, lactate, pyruvate, ketone bodies, ion and/or nutrient levels (e.g., glucose, urea, chloride, sodium, potassium, calcium, iron/ferritin, copper, zinc, magnesium, vitamins, etc.), hormones (e.g., estradiol, follicle-stimulating hormone, aldosterone, progesterone, luteinizing hormone, testosterone, thyroxine, thyrotropin, parathyroid hormone, insulin, glucagon, cortisol, prolactin, etc.), enzymes (e.g., amylase, lactate dehydrogenase, lipase, creatine kinase), lipids (e.g., triglycerides, HDL cholesterol, LDL cholesterol), tumor markers (e.g., alpha fetoprotein, beta human chorionic gonadotrophin, carcinoembryonic antigen, prostate specific antigen, calcitonin), and/or toxins (e.g., lead, ethanol).

Guidewire Sensor Arrangement & Distal Features

Figure 3B:
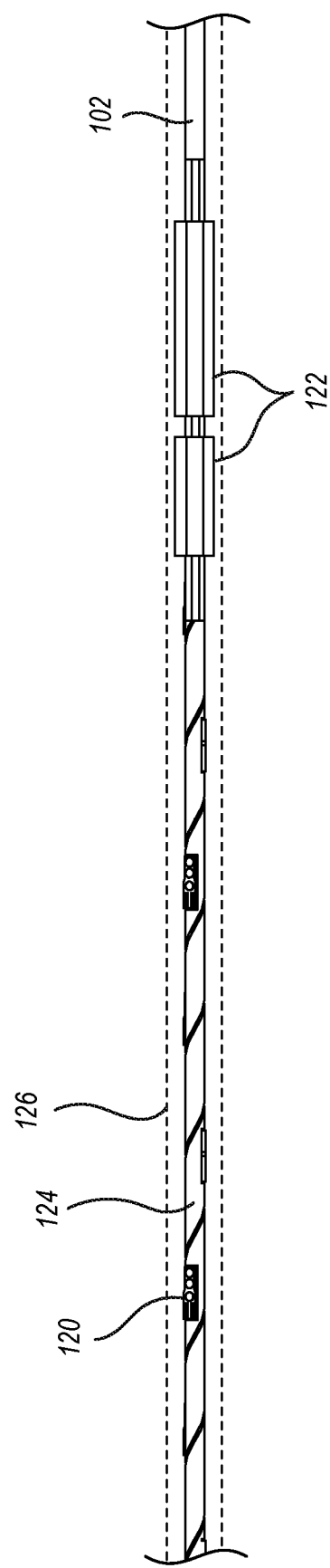
FIG. 3B is an expanded view of a distal section of the guidewire to better illustrate exemplary sensor arrangement on the guidewire.

FIG. 3B illustrates an expanded view of the distal section of the guidewire system 100, showing various sensors arranged thereon. In this embodiment, the sensors include multiple pressure sensors 120 and ultrasound sensors 122. These sensors are positioned on a substrate 124 and the substrate 124 is positioned on the wire 102 in a manner that places the sensors at their respective desired positions. The substrate 124 can be made of a somewhat flexible material (e.g., a suitable medical grade polymer) that allows wrapping, winding, or otherwise positioning the substrate 124 onto the wire 102. The substrate 124 also includes flexible circuitry such as trace lines and/or one or more conductive contacts to conductively couple the sensors to the underlying wire 102. The substrate 124 can form a friction fit with the wire 102, and can additionally or alternatively be mechanically bonded to the wire 102.

Coupling the sensors to the substrate 124 and then placing the substrate 124 on the wire 102 provides several benefits. For example, the substrate 124 can be spread into what is essentially a 2-dimensional layout, which makes it much easier to appropriately position the sensors. The 2-dimensional substrate 124, with sensors coupled thereto, can then be placed on the 3-dimensional cylindrical shape of the wire 102 more readily than placing each sensor separately onto the wire 102. In particular, it is easier to ensure that the various sensors are appropriately positioned relative to one another on the substrate 124 and then to position the substrate 124 onto the wire 102 than to attempt to control relative spacing of each sensor on the 3-dimensional cylindrical shape of the wire 102. One will appreciate, however, that in at least one embodiment, the various sensors can be directly placed on the 3-dimensional wire 102 without the benefit of a 2-dimensional substrate 124. Alternatively, the various sensors can be placed on the substrate after the substrate has been applied to the 3-dimensional wire 102.

The illustrated embodiment also includes an outer member 126 (shown here with hidden lines) that can be positioned over the sensor-containing portion of the wire 102. The outer member 126 may be formed from a suitable medical grade polymer (e.g., polyethylene terephthalate (PET) or polyether block amide (PEBAX)). The outer member 126 can function to further constrain and maintain position of the sensors and/or to smooth over the outer surface for a more uniform outer diameter. The outer member 126 may be applied by shrink-fitting a tube in place, by dip coating, and/or through other manufacturing methods known in the art. A hydrophilic coating may also be added to the outer surface of the device.

Figure 3C:
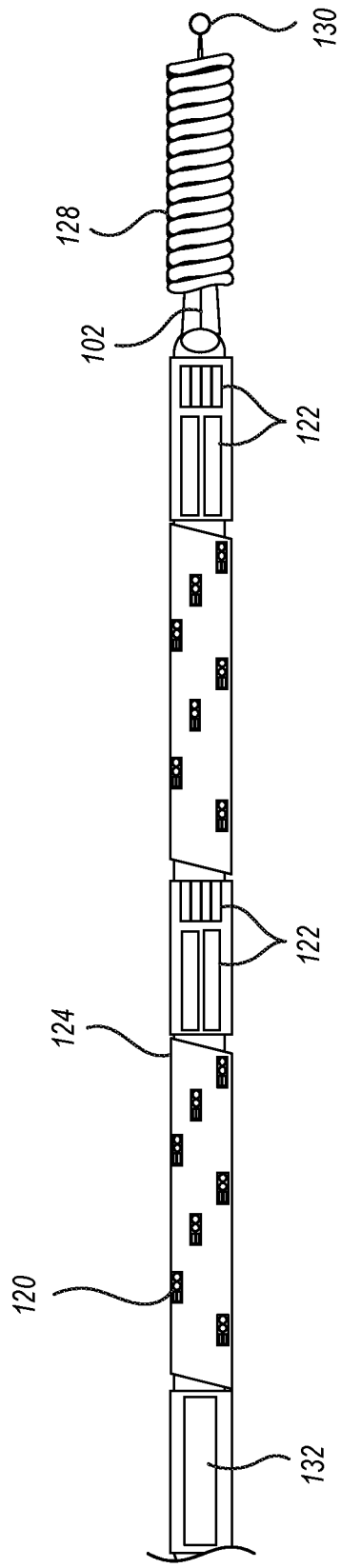
FIG. 3C is an expanded view of a distal section of the guidewire to illustrate additional distal components and features of the device.

FIG. 3C illustrates another, schematic view of the distal section of the guidewire system 100, showing multiple pressure sensors 120 and multiple ultrasound sensors 122 disposed on the substrate 124, which is positioned on the wire 102. As shown, the distal-most section of the device can also include a coil 128 and/or atraumatic tip 130. The coil 128 may be a single coil or multiple connected or interwoven coils. Additionally, or alternatively, a polymer material may be positioned on or applied to the distal section of the wire 102. The atraumatic tip 130 forms a sphere or other curved shape to protect against trauma potentially caused by the distal end of the wire 102. The atraumatic tip 130 may be formed from a polymer adhesive material and/or solder, for example.

As shown, the wire 102 can include a grind profile such that more distal sections of the wire 102 progress to smaller diameters. For typical guidewire sizes (e.g., 0.014 inches, 0.018 inches, 0.024 inches), the wire 102 may progress to a diameter of about 0.002 inches at the distal end. The distal end of the wire 102 may also be flattened to form a standard "ribbon" shape.

The illustrated embodiment also includes an energy harvester 132. The energy harvester is configured to convert injected power into regulated DC voltages suitable for the sensors. The energy harvester 132 can also provide other electrical regulation functions such as cutting power to the sensors during a fault or brownout, for example. Additionally, as used herein and unless specified otherwise, the energy harvester 132 is considered a subcomponent of the one or more sensors 121. As such, unless stated otherwise, references to the one or more sensors 121 also refer to the associated circuitry, such as the energy harvester 132.

Additionally, in at least one embodiment, the energy harvester is configured to provide control functions for the one or more sensors 121. For example, a particular signal can be communicated from the power and data coupling device 104 to the energy harvester. The particular signal may comprise a chirp, an impulse function, or some signal at a particular frequency channel. The energy harvester maps the particular signal to a predetermined command and then acts upon that predetermined command. For example, a particular signal may map to a command to cut DC power to one or more rails that are powering one or more sensors. As such, upon receiving the particular signal, the energy harvester stops providing power to the one or more sensors causing the one or more sensors to turn off. Any number of different signals may be mapped to any number of different commands. Additionally, in at least one embodiment, a circuit other than the energy harvester receives, interprets, and/or acts upon the signals.

Unless stated otherwise, when reference is made to sensors (either generically or to a specific type of sensor) it should be understood to be inclusive of the supporting electronics as well. Supporting electronics may include, for example, power regulators, converters, signal amplifiers, processing components such as application-specified integrated circuits (ASICs), field-programmable gate arrays (FPGAs), and the like. The supporting electronics of the one or more sensors 121 are preferably positioned near the one or more sensors 121 themselves (e.g., at the distal section on the substrate 124). This was beneficially found to reduce signal drift as compared to placing the supporting electronics at the proximal sections of the device. Placing the supporting electronics (e.g., ASICs) at the distal section near the sensors 121, and using the wire 102 itself as the means of transmitting data signals to the proximal end, provides effective signal transmission without the significant drift problems of other approaches.

The length of the wire 102 that includes the substrate 124 (and thus includes sensors) may be about 3 cm to about 30 cm, or more typically about 5 cm to about 15 cm, though these lengths may be varied according to particular application needs. As explained below with respect to the example of FIGS. 4A through 4D, in preferred embodiments the length of the sensor arrangement substantially spans the expected length of lesions/stenoses or other target anatomy. The linear arrangement of pressure sensors 120 can be utilized to provide pressure mapping at targeted anatomy without the need to move the wire 102. Multiple measurements from multiple sensors may be conducted simultaneously and/or continuously. The arrangement of pressure sensors 120 can also be utilized to measure pulse wave velocity (PWV) (e.g., by determining a series of wave peaks and measuring time between peaks) and/or to provide spatial tracking of a pulse waveform.

Methods of Localization Within Target Anatomy

FIGS. 4A through 4D illustrate a sequence showing use of the guidewire system 100 to effectively guide positioning and deployment of a medical device at a targeted anatomical location. In this particular example, the guidewire system 100 is used to properly position a stent 406 at a targeted stenosis 404.

FIG. 4A shows the wire 102 with pressure sensors 120 (other components removed for better visibility) positioned within a vessel 402. The wire 102 is routed through the vessel 402 to a position where the arrangement of pressure sensors 120 span or at least substantially coincide with the stenosis 404. The linear arrangement of the pressure sensors 120 allows the wire 102 to be effectively positioned coincident with the stenosis 404 because the stenosis 404 will cause pressure differences at that portion of the vessel 402, and the user can advance the wire 102 until those pressure differences are read by the sensors 120. For example, where the vessel 402 is a coronary artery, the pressure distal of the stenosis 404 will be somewhat lower than the pressure proximal of the stenosis 404. The wire 102 can be advanced until one or more of the distal-most pressure sensors reach the region of different pressure (e.g., somewhat lower pressure in a coronary vessel stenosis).

The stent 406 is then delivered over the wire 102 toward the stenosis 404. The position of the stent 406 relative to the wire 102 can be determined based on readings from the pressure sensors 120. For example, as the stent 406 is moved distally it will sequentially begin to pass over the pressure sensors 120, causing a change in the pressure reading of the sensors and thereby allowing the user to determine the position of the stent 406 relative to the wire 102.

FIG. 4B shows the stent 406 positioned farther within the vessel 402 to its target location. The delivery catheter 408 is also shown. For stent delivery applications such as shown here, the delivery catheter 408 may be a balloon catheter, or the stent 406 may be a self-expanding stent. Other stent types and stent delivery means as known in the art may be utilized. Proper positioning of the stent 406 is possible because the position of the wire 102 relative to the stenosis 404 is known, and determining where the stent 406 is positioned relative to the wire 102 thus allows determination of the position of the stent 406 relative to the stenosis 404.

Once the stent 406 is determined to be in the proper position relative to the target stenosis 404, the stent 406 may be deployed as shown in FIG. 4C. After deployment, the wire 102 may remain in place for a time during post-stent assessment. The wire 102 may then be retracted from the vessel 402, leaving the stent 406 in place as shown in FIG. 4D.

The guidewire system 100 can therefore provide a localized reference frame (i.e., a reference frame within the localized anatomy of the target) for guiding positioning of a medical device. This is beneficial because the target anatomy is not always static. In vasculature applications, for example, heartbeats cause the vessel to constantly move. The localized reference frame defined by the distal section of the guidewire system 100 moves substantially with the target anatomy in which it is placed, removing many positioning complications and thereby improving the ability to position stents and/or other medical devices.

This localized reference frame is also relatively stable because the wire 102 does not need to be moved to make sequential measurements. That is, the linear arrangement of the sensors 120 allows multiple measurements without the need to "pull back" the wire 102 to make measurements in other positions. Moreover, as described above, the system may be configured to provide multiple measurements from multiple sensors simultaneously, eliminating the need to even do a "virtual pull back" of sequential measurements along the length of sensors.

The procedure illustrated in FIGS. 4A through 4D is one example of using the guidewire system 100 for localization within target anatomy. The guidewire system 100 and/or catheter system 200 may be utilized in other applications where the localization features of the system would be beneficial. For example, localization features described herein may be utilized to aid in proper placement of a PICC catheter or central venous catheter at a targeted site such as the cavoatrial junction.

Sensor Substrate & Application to Guidewire

Figure 5C:
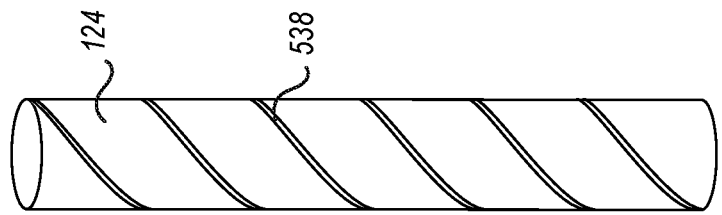
FIGS. 5A-5E illustrate exemplary sensor substrates and various arrangements by which the sensors can be positioned on the guidewire using such substrates.
Figure 5B:
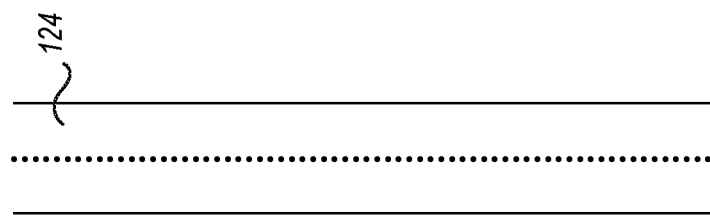
Figure 5A:
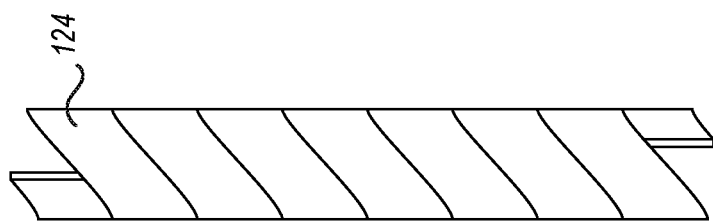

FIGS. 5A-5E illustrate additional exemplary configurations of the substrate 124. FIG. 5A provides an example of the substrate 124 with a structure that allows for spiral wrapping around the wire 102, similar to what is shown in FIGS. 3B and 3C. FIG. 5B shows an example of the substrate 124 with a cut or split within the structure. The substrate 124 of FIG. 5B may also be positioned around the wire 102 until edges meet or overlap at the cut/split. Alternatively, the substrate 124 of FIG. 5B may form a "clamshell" structure with two halves that are placed over the wire 102 and then joined together and/or held in place by an overlying outer member. Although the illustrated cut/split is longitudinal, other embodiments may include other cuts/splits of other shapes, including lateral, curved, helical, and the like. In some embodiments, the cut/split enables a matching interlock and/or set of edges configured to engage with one another when joined.

FIG. 5C shows an example of a substrate 124 with a tube structure and having a cut pattern 538 that allows the tube to be manipulated for placement upon the wire 102. FIG. 5C shows a spiral cut pattern. Other embodiments may additionally or alternatively include other cut patterns (e.g., a series of longitudinal and/or lateral cuts) that allow the tube to be manipulated to enable placement upon the wire 102. Preferably, however, the cut pattern 538 is distributed circumferentially about the tube so as to avoid the formation of preferred bending planes within the tube.

Figure 5D:
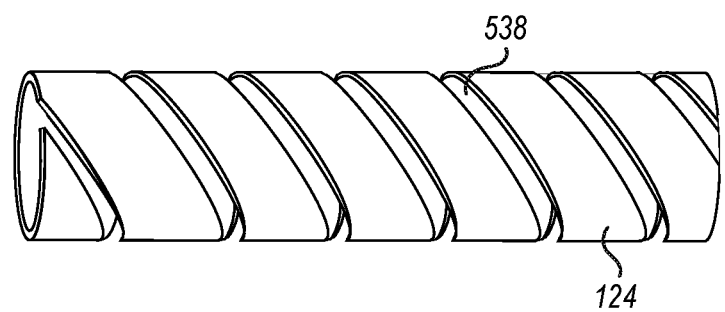
Figure 5E:
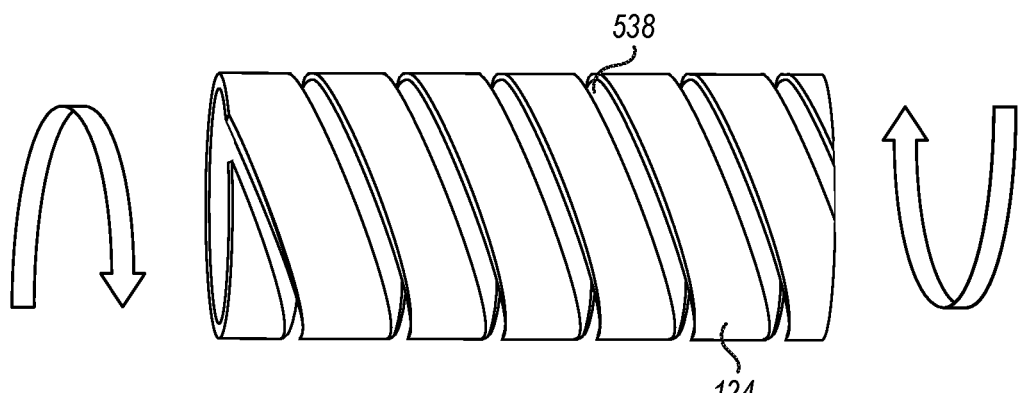

FIGS. 5D and 5E provide an example of how the substrate 124 may be manipulated during placement on the wire 102. FIG. 5D shows the tube structure of the substrate 124 in its default state. By appropriately twisting the ends of the tube, the tube longitudinally shortens and radially expands, as shown in FIG. 5E. In the radially expanded position, the tube can fit over the wire 102 and be positioned in the desired location. Upon removal of the twisting force, the tube then reverts to the default position of FIG. 5D, thereby tightening around the wire 102. In some embodiments, the tube may tighten enough to form a friction fit around the wire 102. As described above, adhesive bonding and/or placement of an outer member may additionally or alternatively function to hold the substrate 124 in place.

FIGS. 6A-6D illustrate a series of steps for applying the sensor substrate 124 to the wire 102. In this example, the substrate 124 has the form of a strip configured to be spirally wrapped around the wire 102 (as in the embodiment shown in FIG. 5A). FIG. 6A shows the substrate 124 laid out in a flat position. The substrate 124 includes a base material 636 (e.g., a suitable medical-grade polymer) and a pair of conductive traces 634. The conductive traces 634 may include, for example, standard conductive copper tracing and/or other conductive materials embedded in or otherwise attached to the base material 636.

In some embodiments, a conductive polymer may be utilized to form the conductive traces 634. For example, the base material 636 may be cut, grooved, or otherwise prepared to receive the conductive polymer in the desired locations, and then the conductive polymer may be applied and (as needed) allowed to cure to form the conductive traces 634.

The conductive traces 634 provide a conductive contact for the sensors (e.g., the illustrated pressure sensors 120, though other sensor types described herein may additionally or alternatively be used) so that the sensors 120 can be placed in conductive communication with the underlying wire 102 once the substrate 124 is applied to the wire 102. For example, the conductive traces 634 may extend from an outer surface of the substrate 124 to an inner surface (in at least one position) to make conductive contact with the underlying wire 102. Alternatively, or additionally, one or more dedicated wire contacts (e.g., at one or both ends of the substrate 124) can be utilized to make conductive contact with the underlying wire 102.

The conductive traces 634 may be formed as one or more continuous and contiguous lines, as shown. Alternatively, one or more discrete sections of conductive material may be included in the substrate 124 for corresponding placement of the sensors, so long as each of the discrete sections are placed in conductive communication with the underlying wire 102.

As shown in FIG. 6B, the sensors 120 are positioned to be offset from the longitudinal axis of the flattened substrate 124. This allows the sensors to be aligned with the longitudinal axis of the wire 102 when the substrate 124 is spirally wrapped around the wire 102, as shown in FIG. 6C. This type of offset may not be necessary for certain sensor types (e.g., sensors that are radially symmetric), but may be utilized where sensor orientation relative to the wire 102 is important. The offset angle may be about 10 to 35 degrees off of the longitudinal axis, for example, though other offset angles may be utilized depending on factors such as wrapping angle of the substrate 124 when applied to the wire 102, desired final orientation of the sensors 120, and the like.

The spacing of the sensors 120 upon the substrate 124 and/or the wrapping angle when applying the substrate 124 to the wire 102 can also be modified to adjust the resulting position and spacing of the sensors 120 relative to the underlying wire 102. For example, the illustrated embodiment shows that each successive sensor 120 is circumferentially offset from adjacent sensors by about 120 degrees. Other circumferential offset angles may be utilized according to design preferences and/or particular application needs. Preferred embodiments include some form of circumferential offset in order to better space the sensors 120 about the circumference of the device and therefore better eliminate circumferential position as a variable in the overall sensor readings.

FIG. 6D illustrates application of the outer member 126 over the substrate 124. As described above, the outer member 126 may be applied using a shrink tube, through dip coating, and/or through other means of applying polymer coatings to guidewires as known in the art. For illustrative purposes, the sensors 120 are shown somewhat above the outer surface of the outer member 126. In most embodiments, the sensors 120 will be flush with the outer surface of the outer member 126.

Imaging Functionality

Figure 7:
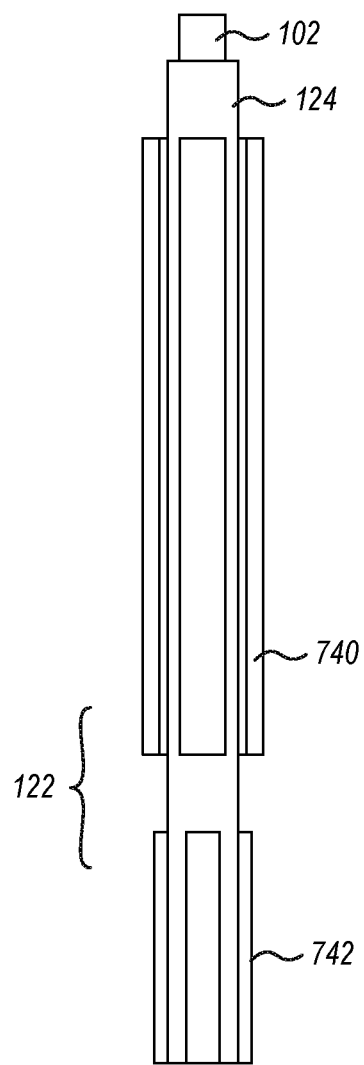
FIG. 7 illustrates a detailed view of an exemplary ultrasound array that may be utilized in the guidewire.

The guidewire system 100 may include one or more sensors for providing imaging. FIG. 7 illustrates an example of an ultrasound sensor 122. As with other sensors described herein, the ultrasound sensor 122 may be placed on a substrate 124 which is then positioned on the wire 102. The illustrated ultrasound sensor 122 includes one or more (preferably multiple) capacitive micromachined ultrasonic transducers (CMUTs) 742 and corresponding supporting electronics in the form of complementary metal oxide semiconductor (CMOS) chips 740. In the illustrated embodiment, each CMUT 742 is associated with its own CMOS chip 740 in a pairwise, 1:1 relationship. Each CMUT 742 and CMOS chip 740 pair works independently to send data signals through the wire 102, without requiring any of the CMOS chips 740 to multiplex multiple signals from separate CMUTs 742.

Ultrasound sensors 122 of the guidewire system 100 may be configured to operate at any appropriate set of frequencies. In some embodiments, the ultrasound sensors 122 are operable with a center frequency of about 5 to about 25 MHz, about 8 to about 20 MHz, about 10 to about 15 MHz, or other ranges using any two of the foregoing values as endpoints. Typical IVUS applications, in contrast, utilize center frequencies of 20 to 40 MHz, or even upwards of 50 MHz. These conventional IVUS applications provide high relative resolution, but have a limited imaging depth of about 5 to 10 mm.

The use of these lower frequencies in the presently described guidewire system 100 provides better imaging depth without overly sacrificing resolution. Because a guidewire is smaller than a typical IVUS catheter, the ultrasound sensor 122 will likely be farther from the targeted anatomy (e.g., vessel wall), and the additional imaging depth is therefore beneficial. The resolutions associated with such frequencies has been found to be sufficient for locating targets (e.g., stenoses) and/or appropriately sizing medical devices (e.g., stents) for deployment.

Some embodiments of guidewire system 100 may additionally or alternatively include other imaging sensors. For example, the guidewire system 100 may include camera devices configured to capture various types of imaging data, including pixel arrays, images, video, or other types of imaging data. The guidewire system 100 may include any imaging device known in the art suitable for positioning at or integration with a distal portion of the system, including a fiber-optic camera, LIDAR system, Raman scattering system, mm wave camera, infrared imaging system, other imaging devices/systems known in the art, or combinations thereof. Image data gathered by such an imaging device may be modified using one or more image enhancing algorithms known in the art.

Power & Data Coupling Device

Figure 8:
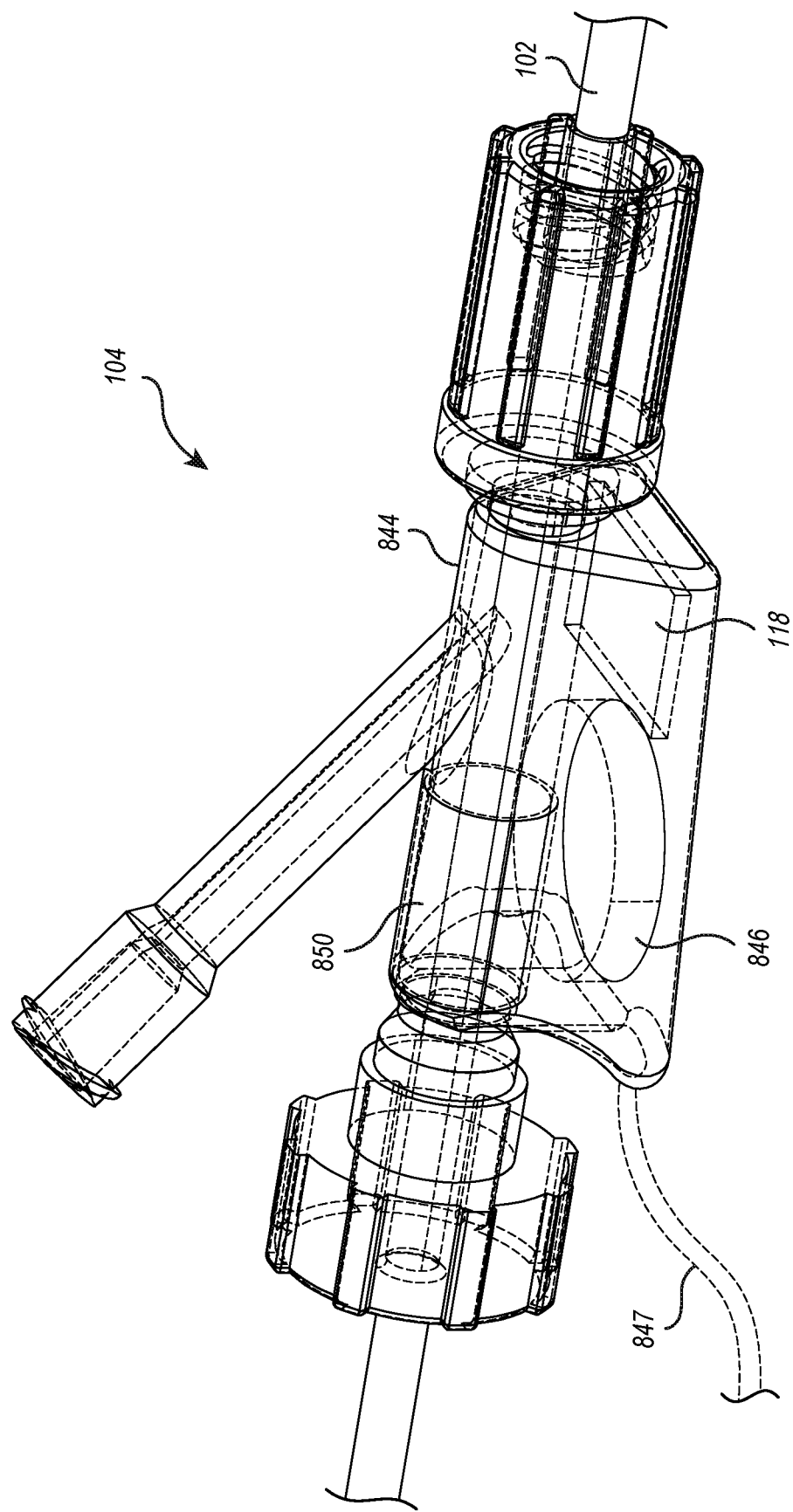
FIG. 8 illustrates a detailed view of an exemplary power and data coupling device.

FIG. 8 provides a detailed view of the exemplary power and data coupling device 104. The coupling device 104 is shown here as a hemostatic valve, but the components and associated functions of the coupling device 104 described herein may be provided by other structures that do not necessarily need to provide valve functionality. However, since hemostatic valves are ubiquitous in guidewire applications, integrating the components of the coupling device 104 into a hemostatic valve is a beneficial implementation.

The illustrated coupling device 104 includes a body 844 that houses the power source (corresponding to power source 114 of FIG. 3A) in the form of a battery 846 and the transmitter 118. The coupling device 104 may additionally or alternatively include a wired power connection 847, though preferred embodiments minimize the use of additional wiring. The coupling device 104 also includes a first conductive surface 850 (shown in this example in the form of a conductive tube) positioned so that the wire 102 passes therethrough when inserted and translated through the coupling device 104.

The illustrated coupling device 104 is configured to function as a capacitive coupler allowing the transfer of power and/or data on and off the wire 102 without requiring direct contact with the wire 102. In particular, the first conductive surface 850 functions as a first conductive surface configured to couple to a second conductive surface (i.e., the wire 102). In operation, the first conductive surface 850 radiates a time-varying electric field to convey power to the wire 102, and includes (or is connected to) a pick-up configured to receive data signals from the wire 102. Because the space between the outer surface of the wire 102 and the inner surface of the first conductive surface 850 will typically be filled with blood, which has relatively decent conductivity, the capacitive couple can be established without requiring particularly high voltages (e.g., 5 to 12 volts is typically sufficient). The first conductive surface 850 is communicatively connected to the transmitter 118 such that the data signals can be transmitted off the coupling device 104 to one or more external devices 110 (see FIGS. 1 and 3A).

The coupling device 104 beneficially allows the wire 102 to remain communicatively coupled to the one or more external device 110 throughout a procedure. For example, a catheter can be passed over the wire 102 and through the coupling device without disrupting the electrical coupling between the first conductive surface 850 and the wire 102. Even though the catheter will pass between the outer surface of the wire 102 and the inner surface of the first conductive surface 850, the capacitive contact is maintained at a level that allows continued transmission of power and data signals. The illustrated coupling device 104 thus allows the user to pass a catheter (or other outer member) over the wire 102 without requiring additional disconnection/reconnection steps and while maintaining constant communication with the sensors at the distal sections of the wire 102. In contrast, systems that require some type of wired connection to the wire in order to pass power and/or data must be temporarily disconnected when a catheter is routed over the wire. In addition to the complications associated with connecting and disconnecting the wire, this means that there will be moments where visualization and/or other data signals from the wire are stopped.

Although the illustrated embodiment includes a first conductive surface 850 in the form of a tube, other embodiments may include a first conductive surface in the form of one or more plates, other concentric or partially-concentric shapes, or other shapes capable of forming sufficient electrical contact with the wire 102. The coupling device 104 may include one or more additional supporting electronic components such as an amplifier for amplification of signals.

The coupling device 104 may be configured to simultaneously provide power to the wire 102 while receiving data signals from the wire 102. In some implementations, the coupling device 104 can provide multiple, different power signals to the wire 102 (e.g., each power signal configured to power a different sensor or different set of sensors) and/or receive multiple, different data signals from the wire 102 (e.g., each data signal from a different sensor or different set of sensors).

In at least one embodiment, the power and data coupling device 104 comprises an indicator for indicating information relating to the operation of the power and data coupling device 104 or the guidewire system 100. The indicator may comprise a sound alert, a visual alert (e.g., a light), a communication to an external device (e.g., external device 110) that performs an alert function and/or any other type of alert. For example, the transmitter 118 may comprise some processing capability that can detect an interruption in power traveling through the power and data coupling device 104 and/or a poor quality of data signals being received by the power and data coupling device 104. In such cases, the power and data coupling device 104 may cause an indication of an alert to be issued in order to notify a user of the issue.

Additional Wire Variations

Figure 9A:
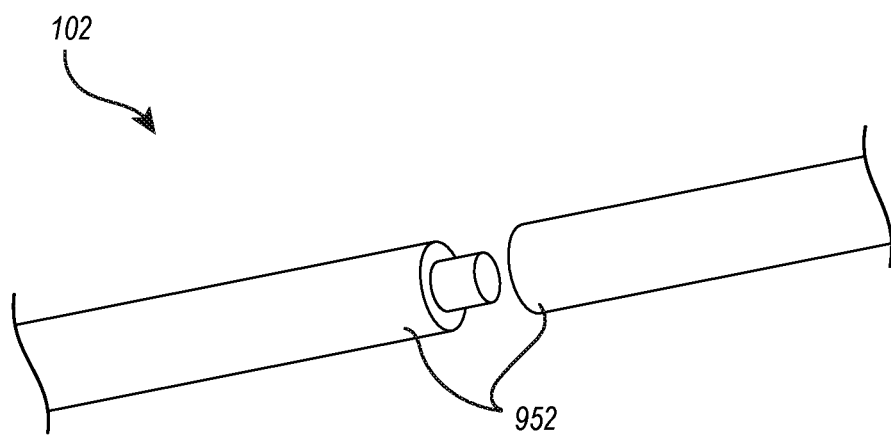
FIGS. 9A and 9B illustrate alternative wire embodiments that may be utilized in a guidewire system as described herein.

FIG. 9A illustrates an example where the wire 102 includes multiple segments 952, such as when an extension is connected to the wire 102. In various use cases, it may be necessary to extend the wire 102 in order to better position and/or manipulate the wire 102 within a patient's body. The depicted segments 952 may be coupled together to form the overall wire 102 through any number of different physical couplings, including, but not limited to, a threaded connection, a magnetic connection, a press-fit connection, a snap connection, an adhesive connection, or combination thereof.

In at least one embodiment, the resulting physical coupling results in a continuous conductive pathway from one segment 952 to the next. As such, due to at least the physical coupling and the electrical coupling, multiple segments 952 assembled together may be jointly considered and referred to as the "wire 102." More specifically, electrical signals applied to a first segment 952 can propagate to other segments 952 of the wire 102. Accordingly, unless stated otherwise, all descriptions of the wire 102 provided herein include embodiments where the wire 102 includes one or more extension wires.

Figure 9B:
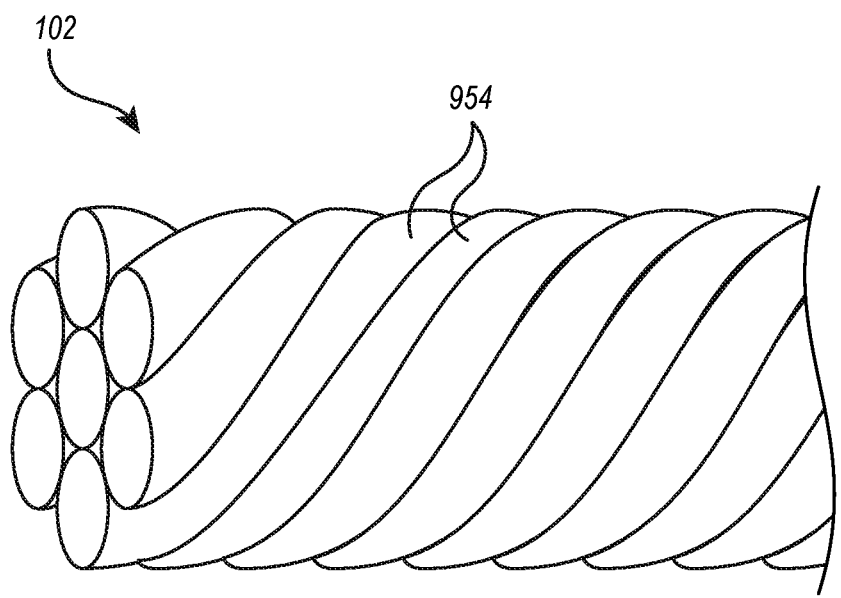

FIG. 9B illustrates another example where the wire 102 includes multiple strands 954 arranged to form a single unitary structure. The number of strands 954 may be varied according to particular application needs. As shown, the strands 954 are twisted, interwoven, or otherwise arranged together to form an overall structure which functions as the wire 102. The separate strands 954 will typically be in conductive contact with one another such that a power or data signal passed to one strand 954 propagates through all the strands 954, and the strands 954 function together as a single wire 102.

Guidewire Tip Localization

Figure 10:
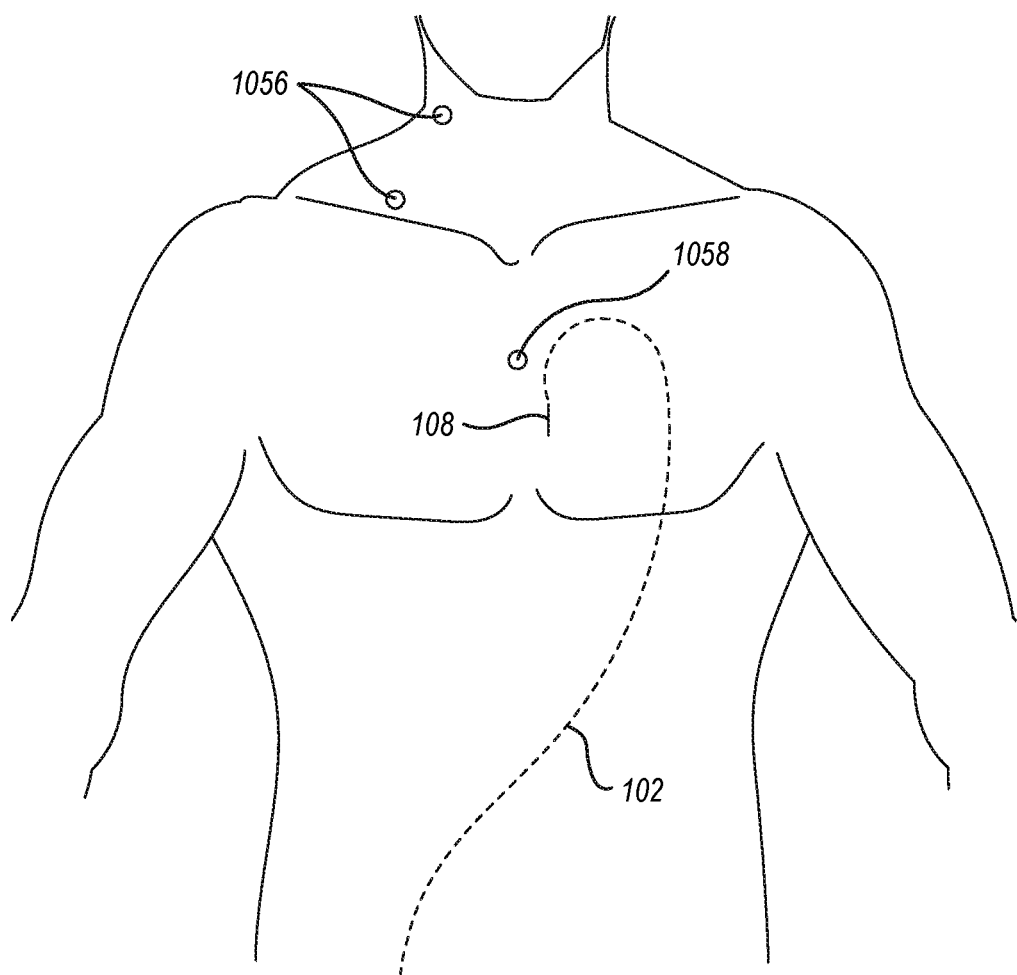
FIG. 10 illustrates systems and methods that provide localization of the guidewire system within the body.

The guidewire system 100 may be utilized in conjunction with one or more detection nodes 1056, 1058 to assist in determining the location of the wire 102 within the body. FIG. 10 shows an example of routing the wire 102 to a patient's targeted coronary artery (e.g., as part of a coronary angioplasty procedure). This example shows a procedure with a coronary artery as target using femoral access, but detection nodes 1056, 1058 may be used in a similar fashion in other procedures involving other target anatomy and/or other access sites.

In the illustrated example, the wire 102 inserted into the body and routed so that the distal end 108 passes into the aortic arch and inferiorly toward a target coronary artery. Detection nodes 1056, 1058 are positioned on the patient at one or more predetermined locations to assist the physician in identifying the position of the distal end 108 of the wire 102. Upon advancing the wire 102 through the vasculature into proximity of a detection node 1056 or 1058, the detection node 1056 or 1058 detects the proximity of the wire 102 via any known detection sensing mechanism known in the art.

For example, the nodes 1056, 1058 may be configured to provide ultrasound transmission and detect ultrasound reflectance. When the coil 128 of the guidewire system 100 passes within the range of a node 1056 or 1058, the node 1056 or 1058 will detect the coil 128 (which typically comprises a highly radiopaque material such as a platinum-iridium alloy) and can be configured to respond by providing an audio signal, visual indicator, and/or by sending a signal to one or more external devices 110 (see FIGS. 1 and 3A) via a wired or wireless connection.

Additionally, or alternatively, the detection nodes 1056, 1058 can be configured to detect an ultrasound signal sent by the guidewire system 100. As described above, the guidewire system 100 can be configured to conduct ultrasound at frequencies lower than in standard IVUS applications. The lower frequencies thus pass farther through surrounding tissues and can be detected by the nodes 1056, 1058. Other detection methods may additionally or alternatively be utilized (e.g., detection of a magnet on the wire 102, the use of radio frequency signals), though it is preferable to use methods that do not require adding more components to the wire 102.

The nodes 1056, 1058 may be arranged at predetermined locations to assist in guiding the wire 102 to the appropriate target location. In the illustrated example, the nodes 1056 are placed at positions corresponding to regions of the vasculature that the wire 102 is not intended to pass through, while node 1058 is positioned along the intended route to the target coronary artery. The nodes 1056 can therefore be configured as warning nodes 1056 that can warn the physician that the wire 102 has passed into an unintended area of the vasculature. In the illustrated procedure, warning nodes 1056 may be placed near a carotid artery and near the subclavian artery, for example. The node 1058 can, in contrast, be configured as a confirmation node 1058 that indicates that the wire is passing through the intended route.

The number of warning nodes 1056 and/or confirmation nodes 1058 may be varied according to particular preferences or application needs. Embodiments that utilize such nodes may thus include one or more of either or both types of nodes.

Additional Computer System Details

Certain methods described herein may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web-based services for communicating back and forth with clients.

Many computers are intended to be used by direct user interaction with the computer. As such, computers have input hardware and software user interfaces to facilitate user interaction. For example, a modern general-purpose computer may include a keyboard, mouse, touchpad, camera, etc. for allowing a user to input data into the computer. In addition, various software user interfaces may be available.

Examples of software user interfaces include graphical user interfaces, text command line-based user interface, function key or hot key user interfaces, and the like.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures, and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Additional Exemplary Aspects

Embodiments of the present disclosure may include, but are not necessarily limited to, features recited in the following clauses:

Clause 1: A medical device, comprising: an elongated wire configured for insertion within a body, the wire having a proximal end and a distal end and being configured to conduct electrical signals; and one or more sensors of one or more sensor types coupled to a distal section of the wire and configured to send and receive the electrical signals via the wire.

Clause 2: The medical device of Clause 1, wherein the wire to which the one or more sensors are coupled is the only wire through which the one or more sensors send and receive the electrical signals.

Clause 3: The medical device of Clause 1 or Clause 2, further comprising one or more outer members disposed over at least a portion of the wire.

Clause 4: The medical device of any one of Clauses 1-3, wherein the one or more sensor types comprise two or more different sensor types.

Clause 5: The medical device of any one of Clauses 1-4, wherein multiple sensors are configured to provide simultaneous measurement of one or more physiological parameters.

Clause 6: The medical device of any one of Clauses 1-5, wherein the one or more sensors have a sampling rate, when active, of 5 seconds or less.

Clause 7: The medical device of any one of Clauses 1-6, wherein the one or more sensors include one or more pressure sensors.

Clause 8: The medical device of Clause 7, wherein the one or more pressure sensors comprise resistive, capacitive, optical, acoustic, optical-acoustic sensors, or a combination thereof.

Clause 9: The medical device of Clause 7 or Clause 8, wherein multiple pressure sensors are longitudinally spaced along a length of a distal section of the wire.

Clause 10: The medical device of Clause 9, wherein the multiple pressure sensors are arranged upon the wire with a circumferential offset applied at each successive pressure sensor or at each successive set of two or more pressure sensors.

Clause 11: The medical device of any one of Clauses 1-10, wherein the one or more sensors include one or more ultrasound sensors.

Clause 12: The medical device of any one of Clauses 1-11, wherein the electrical signals include power signals delivered through the wire to the one or more sensors for powering the one or more sensors.

Clause 13: The medical device of any one of Clauses 1-12, wherein the electrical signals include data signals sent through the wire by the one or more sensors as a result of operation of the one or more sensors.

Clause 14: The medical device of any one of Clauses 1-13, further comprising a proximal device associated with a proximal section of the wire, the proximal device being configured to communicate with the one or more sensors positioned at a distal section of the wire via the electrical signals passed through the wire.

Clause 15: The medical device of Clause 14, wherein the proximal device is configured to send power to the one or more sensors through the wire and to receive data signals from the one or more sensors through the wire.

Clause 16: The medical device of any one of Clauses 1-15, wherein the wire comprises a stranded member having two or more strands associated with one another to form the wire.

Clause 17: The medical device of any one of Clauses 1-16, wherein the wire comprises multiple extensions that are removably attached to one another.

Clause 18: The medical device of any one of Clauses 1-17, wherein the wire has an average outer diameter of at least about 0.003 inches, or at least about 0.005 inches, or at least about 0.008 inches, or at least about 0.010 inches.

Clause 19: The medical device of any one of Clauses 1-18, wherein the one or more sensors are coupled to a substrate, and wherein the substrate is coupled to a distal section of the wire.

Clause 20: The medical device of Clause 19, wherein the substrate is spirally wrapped around the distal section of the wire.

Clause 21: The medical device of Clause 19, wherein the substrate is an elongated tube.

Clause 22: The medical device of Clause 21, wherein the tube includes a cut pattern that enables radial expansion of the tube.

Clause 23: The medical device of any one of Clauses 1-22, wherein the wire comprises a conductive polymer.

Clause 24: The medical device of any one of Clauses 1-23, wherein the wire is configured to be routed through the vasculature of the body.

Clause 25: The medical device of any one of Clauses 1-24, wherein the one or more sensors and supporting electronics corresponding to the one or more sensors are disposed on a distal section of the wire.

Clause 26: A guidewire device for use within an intraluminal space of a body, comprising: an elongated wire having a proximal end and a distal end and being configured to conduct electrical signals; one or more sensors of one or more sensor types coupled to a distal section of the wire; and a proximal device associated with a proximal section of the wire, wherein the proximal device is configured to send power to the one or more sensors through the wire, and wherein the proximal device is configured to receive data signals from the one or more sensors of one or more sensor types through the wire.

Clause 27: A method for using a medical device, the method comprising: positioning, within a luminal space of a body, a first member, the first member comprising an elongated wire; coupling an electrical signal to the wire, the wire having a proximal portion and a distal portion and the wire being configured to conduct electrical signals; and sending and receiving the electrical signal via the wire from one or more sensors of one or more sensor types coupled to the distal portion of the wire.

Clause 28: The method as recited in Clause 27, further comprising: placing a second member over or adjacent to the wire; translating the second member with respect to the wire such that the second member is moved into the body; translating the second member over the one or more sensors; and receiving data signals from the one or more sensors indicating a relative location of the second member within the body with respect to the one or more sensors.

Clause 29: The method as recited in Clause 28, wherein sensors are positioned at multiple longitudinal locations along the distal portion of the wire.

Clause 30: The method as recited in any one of Clauses 27-29, wherein by positioning the wire within the body, the one or more sensors establish a localized reference frame to thereby enable localization of the second member within the localized reference frame.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of using a medical device the method comprising:
  positioning at least one sensor coupled to a first elongated member within a luminal space of a body;
  positioning a second elongated member adjacent a portion of the first elongated member;

translating the second elongated member relative to the at least one sensor;

detecting, with the at least one sensor, a change in a physiological parameter and, based on the detected change in the physiologic parameter, determining a change in position of the second elongated member relative to the at least one sensor; and transmitting a data signal from the at least one sensor responsive to the detected change in the physiologic parameter, the data signal being indicative of the relative location of the second elongated member with respect to the at least one sensor.

2. The method according to claim 1, wherein positioning at least one sensor coupled to a first elongated member within a luminal space of a body includes positioning at least one sensor coupled with a guide wire in a luminal space of a body.

3. The method according to claim 2, wherein positioning a second elongated member adjacent the first elongated member includes positioning a catheter adjacent the first elongated member.

4. The method according to claim 1, wherein the at least one sensor comprises a pressure sensor.

5. The method according to claim 1, further comprising providing the at least one sensor as a plurality of sensors that are longitudinally spaced along a distal portion of the first elongated member.

6. The method according to claim 1, further comprising receiving the data signal from the at least one sensor at a proximal device associated with a proximal portion of the first elongated member.

7. The method according to claim 1, further comprising transporting an implantable device with the second elongated member for placing within the luminal space.

8. The method according to claim 7, further comprising positioning the implantable device at a desired location based on the data signal from the at least one sensor.

9. The method according to claim 8, further comprising implanting the implantable device within the luminal space.

10. The method according to claim 8, further comprising maintaining the first elongated member at a fixed position within the luminal space while the implantable device is being positioned.

11. The method according to claim 1, further comprising receiving the data signal from the at least one sensor at a proximal device associated with a proximal portion of the guidewire.

12. A method of deploying a device within a body, the method comprising:

positioning at least one sensor coupled to a guidewire within a luminal space of a body;

positioning an implantable device carried by a catheter within the luminal space;

translating the catheter and the implantable device relative to the at least one sensor within the luminal space;

detecting, with the at least one sensor, a change in a physiologic parameter and, based on the detected change in the physiologic parameter, determining a position of the implantable device;

transmitting a data signal from the at least one sensor responsive to the detected change in the physiologic parameter, the data signal being indicative of the relative location of the implantable device with respect to the at least one sensor; and positioning the implantable device at a desired location based on the data signal from the at least one sensor.

13. The method according to claim 12, further comprising implanting the implantable device at the desired location within the luminal space.

14. The method according to claim 13, wherein implanting the implantable device includes implanting a stent at the desired location.

15. The method according to claim 12, wherein the at least one sensor comprises a pressure sensor.

16. The method according to claim 12, further comprising providing the at least one sensor as a plurality of sensors that are longitudinally spaced along a distal portion of the guidewire.

* * * * *